(12) United States Patent
Wada et al.

(10) Patent No.: US 7,851,466 B2
(45) Date of Patent: Dec. 14, 2010

(54) PYRIMIDINE COMPOUNDS AND USES THEREOF

(75) Inventors: Yumiko Wada, Billerica, MA (US); Rongzhen Lu, Lincoln, MA (US); Albert Y. Hsia, Cambridge, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 673 days.

(21) Appl. No.: 11/282,926

(22) Filed: Nov. 18, 2005

(65) Prior Publication Data
US 2006/0135518 A1 Jun. 22, 2006

Related U.S. Application Data

(60) Provisional application No. 60/629,505, filed on Nov. 19, 2004.

(51) Int. Cl.
*A61K 31/541* (2006.01)
*A61K 31/5377* (2006.01)
(52) U.S. Cl. ............... 514/222.2; 514/235.2; 514/235.8
(58) Field of Classification Search ............. 514/235.2, 514/235.5, 232.5
See application file for complete search history.

(56) References Cited

U.S. PATENT DOCUMENTS

| | | | |
|---|---|---|---|
| 6,660,733 B2 | 12/2003 | Sun et al. | |
| 6,858,606 B2 | 2/2005 | Sun et al. | |
| 6,958,332 B2 | 10/2005 | Sun et al. | |
| 7,045,517 B2 | 5/2006 | Ono et al. | |
| 7,067,514 B2 | 6/2006 | Ono et al. | |
| 7,122,665 B2 | 10/2006 | Sun et al. | |
| 7,338,951 B2 | 3/2008 | Ono et al. | |
| 7,470,681 B2 * | 12/2008 | Sun et al. | 514/227.8 |
| 7,470,685 B2 * | 12/2008 | Sun et al. | 514/231.5 |
| 2003/0114446 A1 * | 6/2003 | Sun et al. | 514/227.8 |
| 2003/0139403 A1 | 7/2003 | Ono et al. | |
| 2005/0250770 A1 | 11/2005 | Ono et al. | |
| 2005/0250787 A1 | 11/2005 | Sun et al. | |
| 2006/0025409 A1 | 2/2006 | Ono et al. | |
| 2006/0030560 A1 | 2/2006 | Sun et al. | |
| 2006/0063739 A1 | 3/2006 | Sun et al. | |
| 2006/0122209 A1 | 6/2006 | Zhang et al. | |
| 2006/0223996 A1 | 10/2006 | Sun et al. | |
| 2007/0027151 A1 | 2/2007 | Sun et al. | |

FOREIGN PATENT DOCUMENTS

| WO | WO-00/62778 | 10/2000 |
|---|---|---|
| WO | WO-00/78757 | 12/2000 |

OTHER PUBLICATIONS

Vippagunta et al., Crystalline solids, 2001, Advanced Drug Delivery Reviews, 48, pp. 3 and 18.*

Mandred E. Wolff, Burger's Medicinal Chemistry and Drug Discovery, 1995, ImmunoPharmaceutics, Inc., Fifth Edition, vol. I: Principles and Practice, pp. 975-977.*
Vosse et al., Genetic variations in the interleukin-12/interleukin-23 receptor (Beta1) chain, and implications for IL-12 and IL-23 receptor structure and function, 2003, Immunogenetics, 54:817-829.*
Gately et al., Annu. Rev. Immunol. 1998, 16:495-521.
International Search Report and Written Opinion for International Application No. PCT/US05/41928.

* cited by examiner

*Primary Examiner*—Kamal A Saeed
*Assistant Examiner*—Kristin Bianchi
(74) *Attorney, Agent, or Firm*—Edwards Angell Palmer & Dodge LLP; Jeffrey D. Hsi; Weiying Yang

(57) ABSTRACT

This invention features pyrimidine compounds of formula (I):

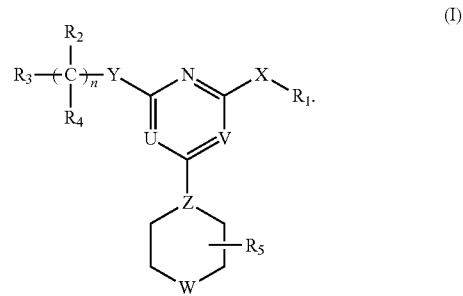

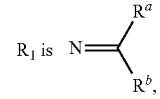

aryl, or heteroaryl; each of $R_2$ and $R_4$, independently, is $R^c$, halogen, nitro, cyano, isothionitro, $SR^c$, or $OR^c$; or $R_2$ and $R_4$, taken together, is carbonyl; $R_3$ is $R^c$, alkenyl, alkynyl, $OR^c$, $OC(O)R^c$, $SO_2R^c$, $S(O)R^c$, $S(O_2)NR^cR^d$, $SR^c$, $NR^cR^d$, $NR^c$-$COR^d$, $NR^cC(O)OR^d$, $NR^cC(O)NR^cR^d$, $NR^cSO_2R^d$, $COR^c$, $C(O)OR^c$, or $C(O)NR^cR^d$; $R_5$ is H or alkyl; n is 0, 1, 2, 3, 4, 5, or 6; X is O, S, S(O), S(O$_2$), or $NR^c$; Y is a covalent bond, $CH_2$, C(O), C=N-$R^c$, C=N-$OR^c$, C=N-$SR^c$, O, S, S(O), S(O$_2$), or $NR^c$; Z is N or CH; one of U and V is N, and the other is $CR^c$; and W is O, S, S(O), S(O$_2$), $NR^c$, or NC(O)$R^c$; in which each of $R^a$ and $R^b$, independently, is H, alkyl, aryl, heteroaryl; and each of $R^c$ and $R^d$, independently, is H, alkyl, aryl, heteroaryl, cyclyl, heterocyclyl, or alkylcarbonyl.

The featured compounds inhibit the production of IL-12, IL-23 and IL-27 and are useful for treating disorders associated with IL-12, IL-23 and IL-27 overproduction or misregulation, such as inflammatory and immune disorders.

24 Claims, 2 Drawing Sheets

PYRIMIDINE COMPOUNDS AND USES THEREOF

RELATED APPLICATIONS

This application claims the benefit of U.S. provisional patent application Ser. No. 60/629,505, filed Nov. 19, 2004, the disclosure of which is incorporated herein in its entirety by this reference.

BACKGROUND

Interleukin-12 (IL-12) is a heterodimeric cytokine (p70) which plays a key role in immune responses by bridging innate resistance and antigen-specific adaptive immunity. Trinchieri (1993) *Immunol Today* 14: 335. For example, it promotes type 1 T helper cell (Th1) responses and, hence, cell-mediated immunity. (See Chan et al. (1991) *J Exp Med* 173: 869; Seder et al. (1993) *Proc Natl Acad Sci USA* 90: 10188; Manetti et al. (1993) *J Exp Med* 177: 1199; and Hsieh et al. (1993) *Science* 260: 547, the entire teachings of each of these references are incorporated here in by reference). IL-12 is composed of two, disulfide linked, independently regulated subunits, p35 and p40. IL-12 is produced by phagocytic cells and antigen presenting cells, in particular, macrophages and dendritic cells, upon stimulation with bacteria, bacterial products such as lipopolysaccharide (LPS), and intracellular parasites. The well-documented biological functions of IL-12 are induction of interferon-γ (INF-γ) expression from T and NK cells and differentiation of naïve T cells toward the Th1 T lymphocyte type. IFN-γ, expression of which is induced by IL-12, is a strong and selective enhancer of IL-12 production from monocytes and macrophages.

The cytokine IL-23 is a heterodimer composed of a p19 subunit and the same p40 subunit as IL-12. Exposure of activated CD4+ T cells to IL-23 causes them to develop into a novel T cell subset (Th$_{IL-17}$ cells) characterized by the production of IL-17 (Langrish, et al., *Immunological Reviews* (2004), 202:96-105, the entire teachings of which are incorporated herein by reference). IL-17 has been implicated in a number of autoimmune diseases. For example, IL-23 knock out mice have a severely impaired IL-17 response and are resistant to experimental autoimmune encephalitis (EAE) (a model for multiple sclerosis) and collagen-induced arthritis. In addition, IL-17 has been shown to increase neutrophil activity in the lungs of patients with acute and chronic asthma and in patients with chronic obstructive pulmonary disease (COPD).

IL-27 is formed by the association of EBI3, a polypeptide related to the p40 subunit of IL-12, and p28, a protein related to the p35 subunit of IL-12. IL-27 promotes the growth of T cells and, like IL-12, is thought to play a role in the differentiation of naïve T cells to Th1 cells. Pflanz et al., *Immunity* (2002), 16:779-790.

It has been suggested that, particularly in chronic diseases in which there is ongoing production of IFN-γ, IL-12 production is augmented by IFN-γ. It is presumed that after an infective or inflammatory stimulus that provokes IL-12 production, the powerful feedback loop promotes IL-12-induced IFN-γ to further augment IL-12 production, leading to consequent excessive production of pro-inflammatory cytokines. In particular, activated CD4+ T cells produced by this process when exposed to IL-23 differentiate into a subset of T cells that produce the pro-inflammatory cytokine, IL-17. Furthermore, it has been suggested that IL-27 induces the expression of T-bet, a major Th1-specific transcription factor, and its downstream target IL-12R β2, independently of IFN-γ. In addition, IL-27 suppresses the expression of GATA-3. GATA-3 inhibits Th1 development and causes loss of IL-12 signaling through suppression of IL-12R β2 and Stat4 expression. Lucas et al., *PNAS* (2003), 100:15047-15052.

IL-12, IL-23 and IL-27, as well as IL-17, play a critical role in many autoimmune diseases including, but not limited to, multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroiditis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, polymyositis, dermatomyositis, spondyloarthropathies, ankylosing spondylitis, Sjogren's syndrome and graft-versus-host disease. (See, for example, Gately et al. (1998) *Annu Rev Immunol.* 16: 495; and Abbas et al. (1996) *Nature* 383: 787, the entire teachings of which are incorporated by reference.)

Inhibiting IL-12, IL-23 and IL-27 is an approach to treating autoimmune and inflammatory disorders by inhibiting the production of Th1 and Th$_{IL-17}$ cells and thereby down-regulating pro-inflammatory cytokines such as IL-17. (Trembleau et al. (1995) *Immunol. Today* 16: 383; and Adorini et al. (1997) *Chem. Immunol.* 68: 175; and Langrish, et al., *Immunological Reviews* (2004), 202:96-105, the entire teachings of both of these articles are incorporated herein by reference). Therefore, compounds that inhibit the production of IL-12, IL-23 and IL-27 are useful for treating autoimmune and inflammatory disorders.

SUMMARY

The present invention relates to compounds that inhibit the production of IL-12, IL-23, and IL-27 and are useful in treating autoimmune and inflammatory disorders. In one aspect, this invention features pyrimidine compounds of formula (I):

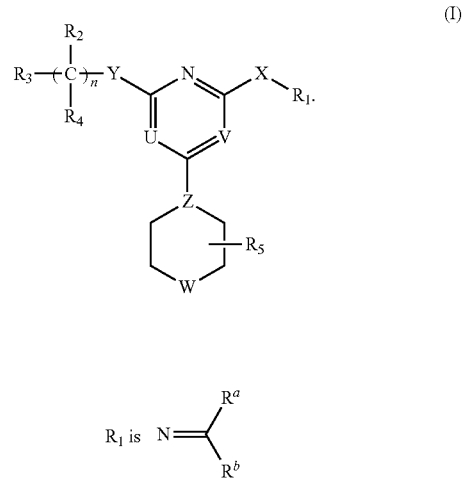

[referred to hereinafter as NC($R^aR^b$)], aryl, or heteroaryl; each of $R_2$ and $R_4$, independently, is $R^c$, halogen, nitro, cyano, isothionitro, $SR^c$, or $OR^c$; or $R_2$ and $R_4$, taken together, is carbonyl; $R_3$ is $R^c$, alkenyl, alkynyl, $OR^c$, $OC(O)R^c$, $SO_2R^c$, $S(O)R^c$, $S(O_2)NR^cR^d$, $SR^c$, $NR^cR^d$, $NR^cCOR^d$, $NR^cC(O)OR^d$, $NR^cC(O)NR^cR^d$, $NR^cSO_2R^d$, $COR^c$, $C(O)OR^c$, or $C(O)NR^cR^d$; $R_5$ is H or alkyl; n is 0, 1, 2, 3, 4, 5, or 6; X is O, S, S(O), S($O_2$), or $NR^c$; Y is a covalent bond, $CH_2$, C(O), C=N—$R^c$, C=N—$OR^c$, C=N—$SR^c$, O, S, S(O), S($O_2$), or $NR^c$; Z is N or CH; one of U and V is N, and the other is $CR^c$; and W is O, S, S(O), S($O_2$), $NR^c$, or $NC(O)R^c$; in which each of $R^a$ and $R^b$, independently, is H, alkyl, aryl, heteroaryl; and each of $R^c$ and $R^d$, independently, is H, alkyl, aryl, heteroaryl, cyclyl, heterocyclyl, or alkylcarbonyl. Also note that when n is 2 or greater, the just-described heteroaryl compound may have two or more different $C(R^2R^4)$ moieties. The same rule applies to other similar situations.

Referring to formula (I), a subset of the pyrimidine compounds of this invention is featured by that $R^1$ is $NC(R^aR^b)$. In these compounds, U can be N, V can be CH, Z can be N, and W can be O. In addition, X can be $NR^c$; $R^c$ can be H, methyl, ethyl, or acetyl; Y can be O or $CH_2$, and n can be 0, 1, 2, 3, or 4. In some embodiments, $R_3$ is aryl, heteroaryl (e.g., pyridinyl), $OR^c$, $SR^c$, $C(O)OR^c$, or $C(O)NR^cR^d$. In other embodiments, $R_3$ is

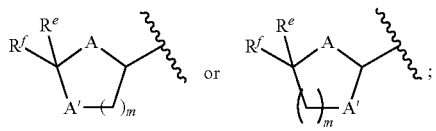

in which each of A and A', independently, is O, S, or NH; each of $R^e$ and $R^f$, independently, is H, alkyl, aryl, or heteroaryl; and m is 1 or 2.

In this subset of pyrimidine compounds, $R^a$ or $R^b$, preferably, is

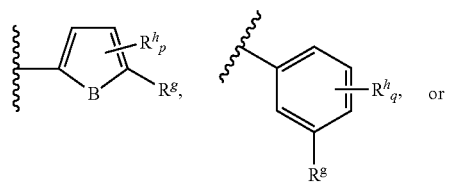

in which B is $NR^i$, O, or S; B' is N or $CR^i$; $R^g$ is H, alkyl, or alkoxyl; $R^h$ is halogen, $NO_2$, CN, alkyl, aryl, heteroaryl, $OR^c$, $OC(O)R^c$, $SO_2R^c$, $S(O)R^c$, $S(O_2)NR^cR^d$, $SR^c$, $NR^cR^d$, $NR^c$-$COR^d$, $NR^cC(O)OR^d$, $NR^cC(O)NR^cR^d$, $NR^cSO_2R^d$, $COR^c$, $C(O)OR^c$, or $C(O)NR^cR^d$; $R^i$ is H, alkyl, or alkylcarbonyl; p is 0, 1, or 2; and q is 0, 1, 2, 3, or 4. Preferably, B is $NR^i$; B' is CH; $R^g$ is H, methyl, ethyl, propyl, cyclopropyl, methoxy, or ethoxy; $R^h$ is F, Cl, CN, methyl, methoxy, ethoxy, OC(O)$CH_3$, $OC(O)C_2H_5$, C(O)OH, $C(O)OC_2H_5$, $C(O)NH_2$, NHC(O)$CH_3$, or $S(O_2)NH_2$; $R^i$ is H, methyl, ethyl, or acetyl; and q is 0, 1, or 2.

Another subset of the pyrimidine compounds of this invention is featured by that $R^1$ is aryl or heteroaryl. In these compounds, U can be N, V can be CH, Z can be N, and W can be O. In addition, X can be $NR^c$; $R^c$ can be H, methyl, ethyl, or acetyl; Y can be O or $CH_2$, and n can be 0, 1, 2, 3, or 4. In some embodiments, $R_3$ is aryl, heteroaryl (e.g., pyridinyl), $OR^c$, $SR^c$, $C(O)OR^c$, or $C(O)NR^cR^d$. In other embodiments, $R_3$ is

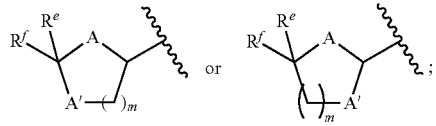

in which each of A and A', independently, is O, S, or NH; each of $R^e$ and $R^f$, independently, is H, alkyl, aryl or heteroaryl; and m is 1 or 2.

In this second subset of pyrimidine compounds, $R_1$, preferably, is

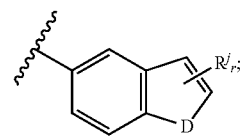

in which D is O, S, or $NR^m$; $R^j$ is benzo, halogen, CN, hydroxyl, alkyl, aryl, heteroaryl, alkoxyl, aryloxyl, or heteroaryloxyl; $R^m$ is H, alkyl, or alkylcarbonyl; and r is 0, 1, or 2. Preferably, $R_1$ is

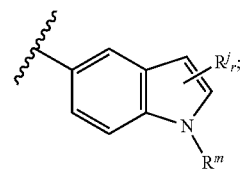

and $R^j$ is methyl, ethyl, propyl, or benzo; and r can be 1 or 2.

Set forth below are exemplary compounds of this invention:

Compound 1:

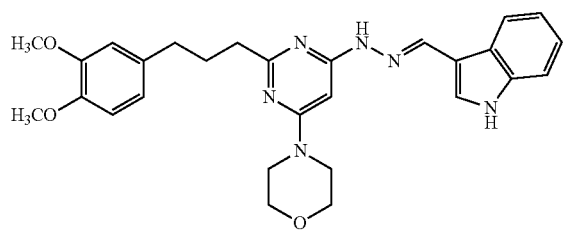

-continued
Compound 2:
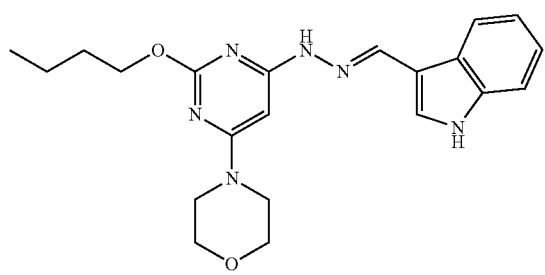
Compound 3:
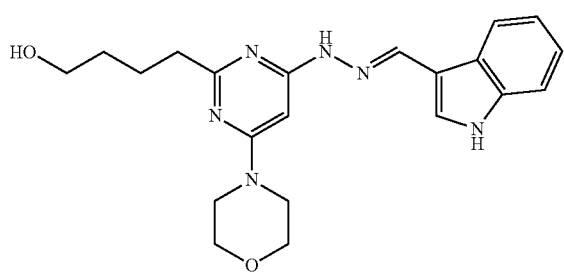
Compound 4:
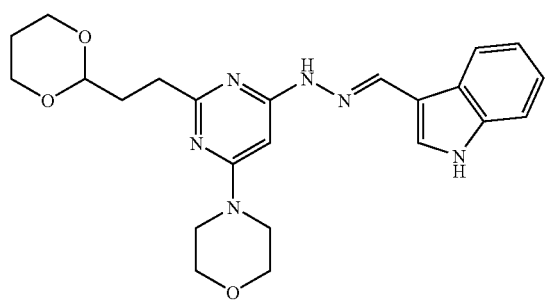
Compound 5:
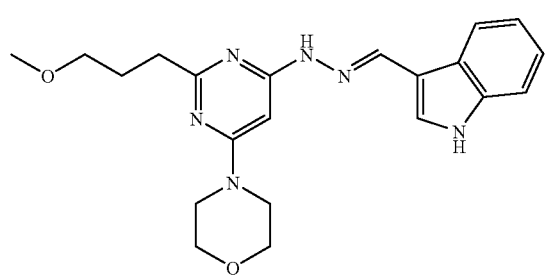
Compound 6:
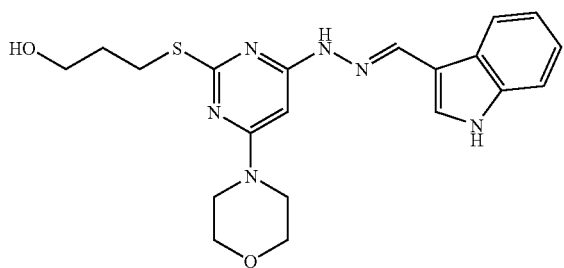
-continued
Compound 7:
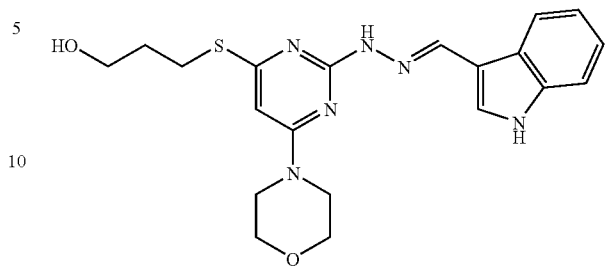
Compound 8:
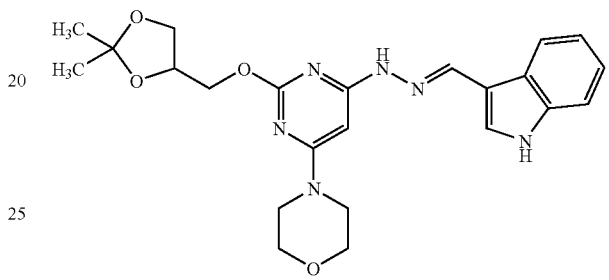
Compound 9:
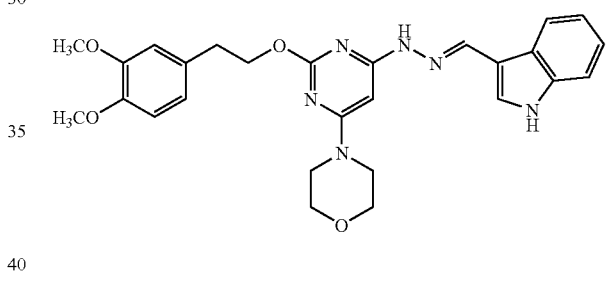
Compound 10:
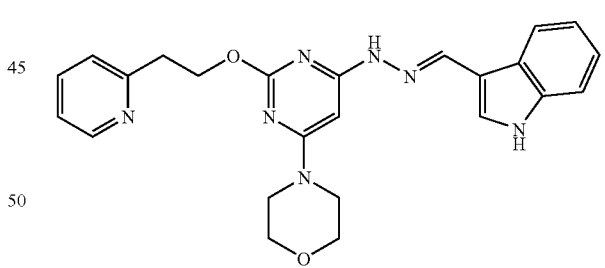
Compound 11:
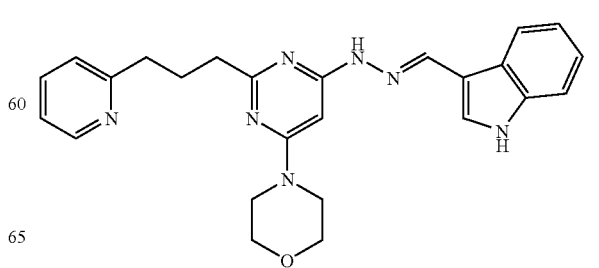

-continued
Compound 12:
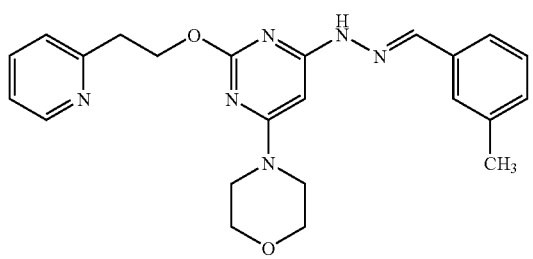
Compound 13:
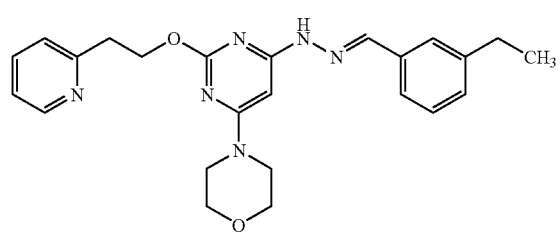
Compound 14:
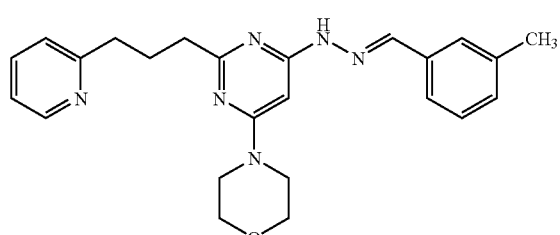
Compound 15:
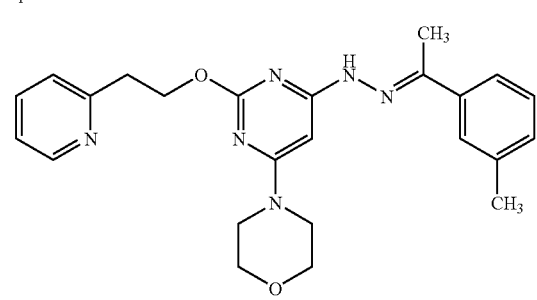
Compound 16:
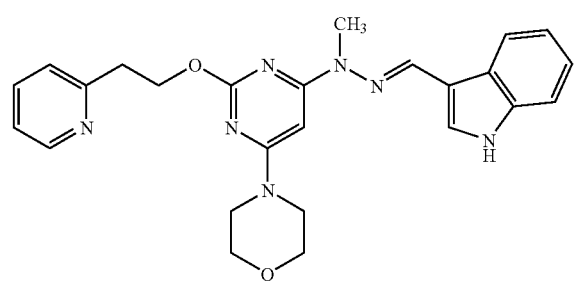
-continued
Compound 17:
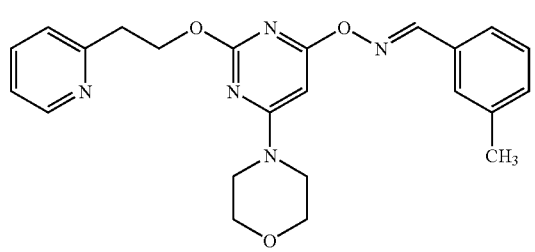
Compound 18:
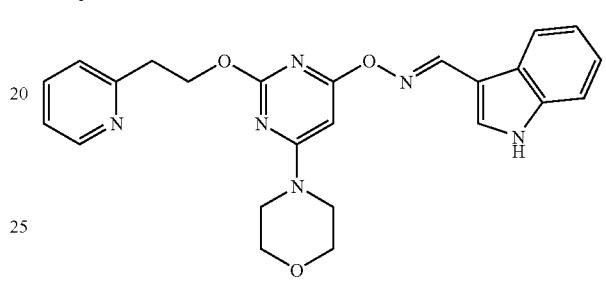
Compound 19:
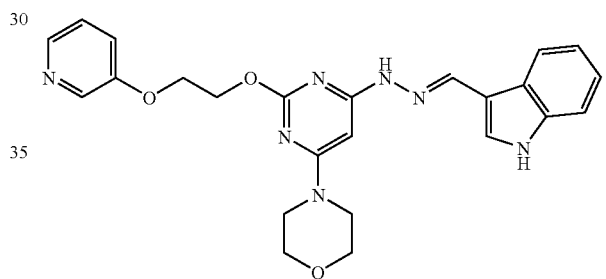
Compound 20:
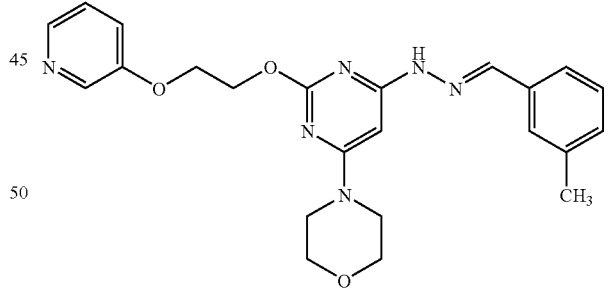
Compound 21:
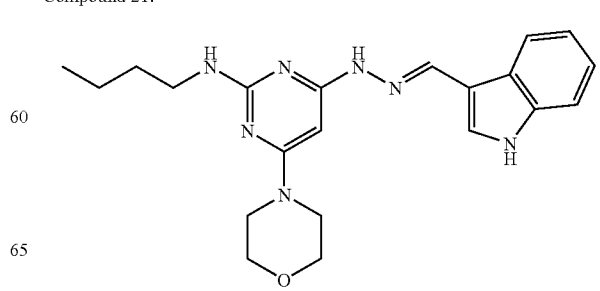

-continued

Compound 22:

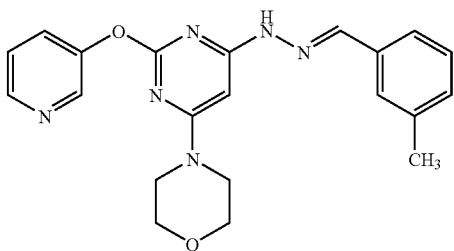

Compound 23:

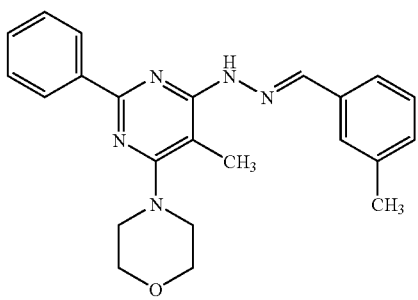

Compound 24:

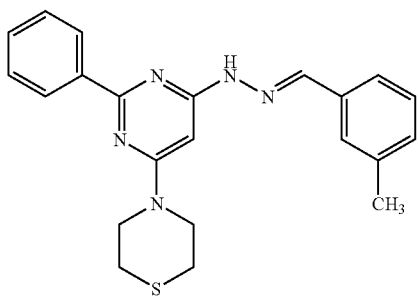

Compound 25:

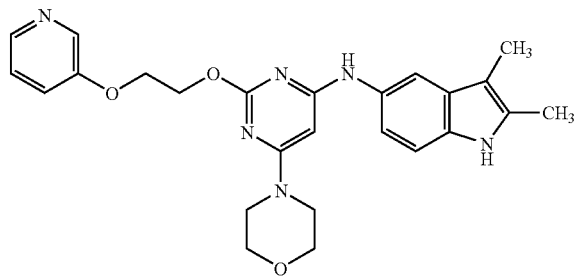

Compound 26:

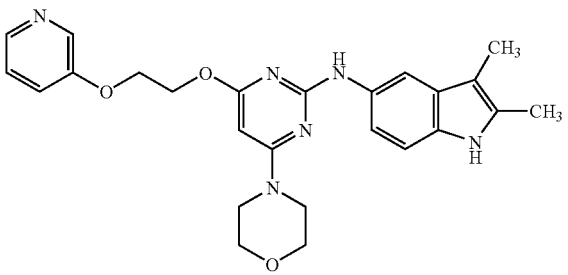

-continued

Compound 27:

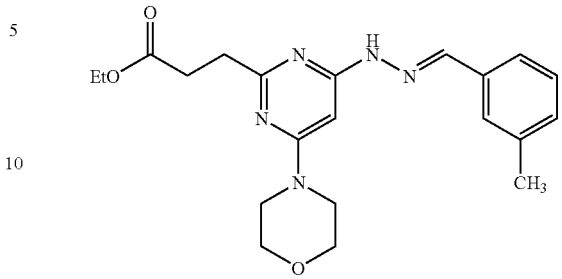

In another aspect, this invention features a pharmaceutical composition that contains a pharmaceutically acceptable carrier and an effective amount of at least one of the pyrimidine compounds of this invention, or pharmaceutically acceptable salt, solvate, clathrate, hydrate, polymorph, or prodrug thereof.

In another aspect, the present invention features a method for treating or preventing an autoimmune or inflammatory disorder in a subject, wherein the autoimmune or inflammatory disorder is selected from the group consisting of ankylosing spondilitis, gastric ulcer, ulcerative colitis, seronegative arthropathies, systemic lupus erythematosis, antiphospholipid syndrome, iridocyclitis/uveitis/optic neuritis, idiopathic pulmonary fibrosis, inflammatory pulmonary syndrome, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, neutropenic fever, urosepsis, meningococcemia, trauma/hemorrhage, burns, ionizing radiation exposure, acute pancreatitis, adult respiratory distress syndrome, alcohol-induced hepatitis, chronic inflammatory pathologies, sarcoidosis, sickle cell anemia, type II diabetes, nephrosis, atopic diseases, hypersentitity reactions, allergic rhinitis, hay fever, perennial rhinitis, conjunctivitis, endometriosis, asthma, urticaria, systemic anaphalaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, asthma, myasthenia gravis, antibody-meditated cytotoxicity, type III hypersensitivity reactions, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, alopecia, nephrotic syndrome, nephritis, glomerular nephritis, acute renal failure, hemodialysis, uremia, toxicity, preeclampsia, pemphigus vulgaris, chronic salicylate intoxication, idiopathic thrombocytopenic purpura, autoimmune meningitis, myasthenia gravis, autoimmune thyroiditis, Sjogren's Syndrome, alopecia areata, allergic responses due to arthropod bite reactions, aphthous ulcer, iritis, conjunctivitis, keratoconjunctivitis, cutaneous lupus erythematosus, scleroderma, vaginitis, proctitis, drug eruptions, leprosy reversal reactions, erythema nodosum leprosum, autoimmune uveitis, allergic encephalomyelitis, aplastic anemia, pure red cell anemia, idiopathic thrombocytopenia, polychondritis, Wegener's granulomatosis, chronic active hepatitis, Graves ophthalmopathy, primary biliary cirrhosis, uveitis posterior and interstitial lung fibrosis. The method comprises administering to a subject in need thereof a compound of formula I, or any formula disclosed herein, or pharmaceutically acceptable salt, solvate, clathrate, hydrate, polymorph, or prodrug thereof.

In another aspect, the present invention features a method for treating or preventing an autoimmune or inflammatory disorder in a subject, wherein the autoimmune or inflammatory disorder is selected from the group consisting of juvenile rheumatoid arthritis, systemic onset juvenile rheumatoid arthritis, psoriatic arthritis, ankylosing spondilitis, osteoarthritis, and Lyme arthritis. The method comprises administering to a subject in need thereof a compound of formula I, or an formula disclosed herein, or pharmaceutically acceptable salt, solvate, clathrate, hydrate, polymorph, or prodrug thereof.

In another aspect, the present invention features a method for treating or preventing an autoimmune or inflammatory disorder in a subject, wherein the autoimmune or inflammatory disorder is selected from the group consisting of asthma, neonatal chronic lung disease, or chronic obstructive pulmonary disease. The method comprises administering to a subject in need thereof a compound of formula I, or any formula disclosed herein, or pharmaceutically acceptable salt, solvate, clathrate, hydrate, polymorph, or prodrug thereof. As disclosed above, IL-23 stimulates activated CD4$^+$ T cells to develop into a novel T cell subset characterized by the production of IL-17. IL-17 has been shown to increase neutrophil activity in the lungs in patients with severe asthma and in patients with chronic obstructive pulmonary disease.

In one embodiment, this invention features a method of inhibiting IL-23, IL-27, and/or IL-12 production in a subject, comprising administering to the subject an effective amount of a compound of formula I, or any formula disclosed herein, or pharmaceutically acceptable salt, solvate, clathrate, hydrate, polymorph, or prodrug thereof.

In another embodiment, the invention features a method of inhibiting development or proliferation of Th$_{IL-17}$ cells, comprising administering to a subject in need thereof a compound of formula I, or any formula disclosed herein, or pharmaceutically acceptable salt, solvate, clathrate, hydrate, polymorph, or prodrug thereof. In one embodiment, the method further comprises inhibiting the production of IL-17.

In another embodiment, the invention features a method of inhibiting development or proliferation of Th1 cells, comprising administering to a subject in need thereof a compound of formula I, or any formula disclosed herein, or pharmaceutically acceptable salt, solvate, clathrate, hydrate, polymorph, or prodrug thereof. In one embodiment, the method further comprises inhibiting the production of IL-17.

In addition, some of the pyrimidine compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such forms are included in the invention.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
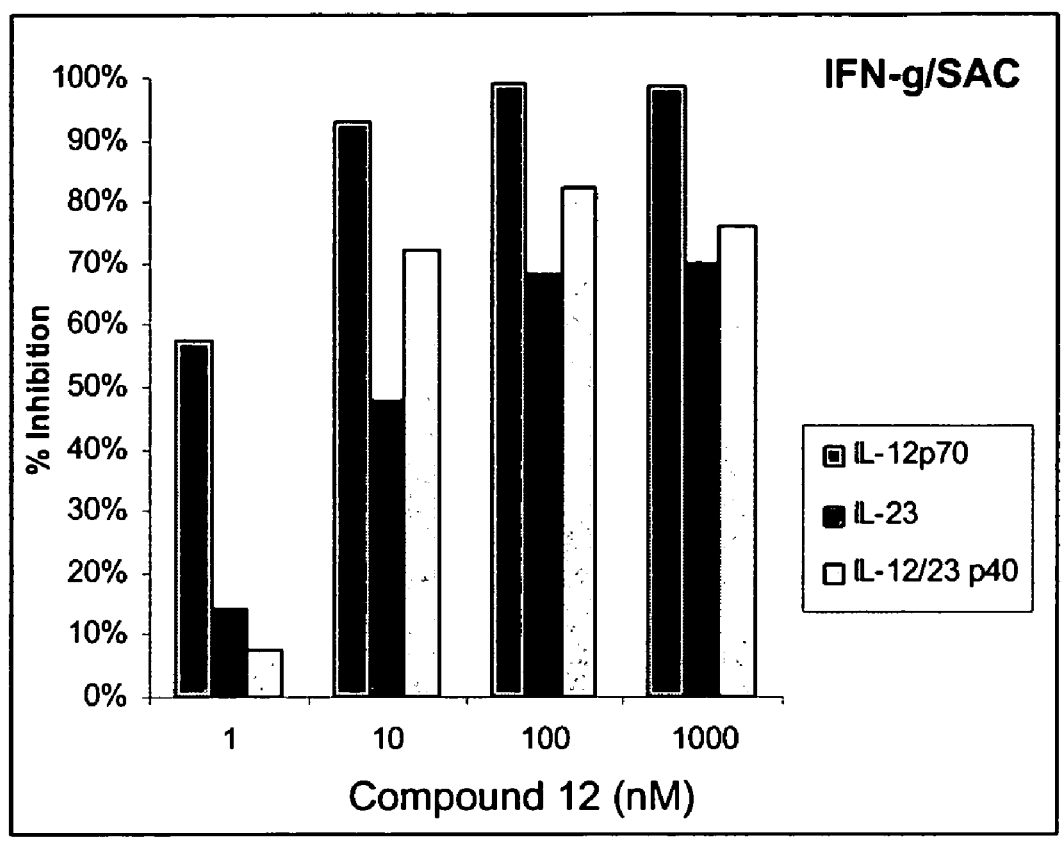
FIG. 1 is a graph showing the percent inhibition of IL-12, IL-23 and the p40 subunit of IL-12 and IL-23 by Compound 12 in human peripheral blood mononuclear cells after stimulation with S. aureus Cowan I (SAC) in the presence of IFN-γ.

Alkyl, alkenyl, alkynyl, aryl, heteroaryl (e.g., pyridinyl), cyclyl, heterocyclyl mentioned above include both substituted and unsubstituted moieties. The term "substituted" refers to one or more substituents (which may be the same or different), each replacing a hydrogen atom. Examples of substituents include, but are not limited to, halogen, hydroxyl, amino, alkylamino, arylamino, dialkylamino, diarylamino, cyano, nitro, mercapto, alkylcarbonyl, carbamido, carbamyl, carboxyl, thioureido, thiocyanato, sulfoamido, $C_1$~$C_6$ alkyl, $C_1$~$C_6$ alkenyl, $C_1$~$C_6$ alkoxy, aryl, heteroaryl, cyclyl, heterocyclyl, wherein alkyl, alkenyl, alkoxy, aryl, heteroaryl, cyclyl, and heterocyclyl are optionally substituted with $C_1$~$C_6$ alkyl, aryl, heteroaryl, halogen, hydroxyl, amino, mercapto, cyano, or nitro.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The sp$^2$ or sp carbons of an alkenyl group and an alkynyl group, respectively, may optionally be the point of attachment of the alkenyl or alkynyl groups.

The term "cyclyl" refers to a hydrocarbon 3-8 membered monocyclic or 7-14 membered bicyclic ring system having at least one non-aromatic ring which may optionally have some degree of saturation. Cyclyl groups may be optionally substituted with one or more substituents. In one embodiment, 0, 1, 2, 3, or 4 atoms of each ring of a cyclyl group may be substituted by a substituent. Representative examples of cyclyl group include cyclopropyl, cyclopentyl, cyclohexyl, cyclobutyl, cycloheptyl, cyclooctyl, cyclononyl, cyclodecyl, cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon ring system having at least one aromatic ring. Typically, a monocyclic aryl will have from 5 to 8 carbon atom ring members; a bicyclic ary will have from 7 to 14 carbon atom ring members, and a tricyclic aryl will have 11-14 carbon atom ring members. Examples of aryl moieties include, but are not limited to, phenyl, naphthyl, anthracenyl, fluorenyl, indenyl, azulenyl, pyrenyl, and the like.

The term "heterocyclyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system may have some degree of saturation. Heterocyclyl groups may be optionally substituted with one or more substituents. In one embodiment, 0, 1, 2, 3, or 4 atoms of each ring of a heterocyclyl group may be substituted by a substituent. Representative heterocyclyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydrofuranyl, tetrahydrothienyl, thiirenyl, thiadiazirinyl, dioxazolyl, 1,3-oxathiolyl, 1,3-dioxolyl, 1,3-dithiolyl, oxathiazinyl, dioxazinyl, dithiazinyl, oxadiazinyl, thiadiazinyl, oxazinyl, thiazinyl, 1,4-oxathiin, 1,4-dioxin, 1,4-dithiin, 1H-pyranyl, oxathiepinyl, 5H-1,4-dioxepinyl, 5H-1,4-dithiepinyl, 6H-isoxazolo[2,3-d]1,2,4-oxadiazolyl, 7aH-oxazolo[3,2-d]1,2,4-oxadiazolyl, and the like.

The term "heteroaryl" refers to a hydrocarbon ring system having at least one aromatic ring which contains at least one heteroatom such as O, N, or S. Typically, a moncyclic heteroaryl has 5-8 ring members, a bicyclic heteroaryl has 7-12 ring members, and a tricyclic heteroaryl has 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like. Examples of heteroaryl moieties include, but are not limited to, furyl, fluorenyl, pyrrolyl, thienyl, oxazolyl, imidazolyl, thiazolyl, pyridinyl, pyrimidinyl, quinazolinyl, and indolyl.

The compounds of this invention include the compounds themselves, as well as their salts, solvate, clathrate, hydrate, polymorph, or prodrugs, if applicable. As used herein, the term "pharmaceutically acceptable salt," is a salt formed from, for example, an acid and a basic group of a compound of any one of the formulae disclosed herein. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, which further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO₂, —ONO, or —ONO₂ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed).

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the terms "animal", "subject" and "patient", include, but are not limited to, a cow, monkey, horse, sheep, pig, chicken, turkey, quail, cat, dog, mouse, rat, rabbit, guinea pig and human (preferably, a human).

As used herein, the term "a subject in need thereof" refers to a subject suffering from an autoimmune or inflammatory disorder or who has a predisposition (e.g., a genetic predisposition) to develop an autoimmune or inflammatory disorder. In addition, subjects that have had an autoimmune or inflammatory disorder that is in remission may be in need of treatment with one or more compounds of the invention, or a pharmaceutically acceptable salt, solvate, clathrate, hydrate, polymorph, or prodrug thereof, to prevent a relapse of the autoimmune or inflammatory disorder.

The compounds described above can be prepared by methods well known in the art, as well as by the synthetic routes disclosed herein and described in U.S. Pat. Nos. 6,693,097, 6,660,733, 6,858,606 and in U.S. Provisional Application No. 60/626,609, the entire teaching of each of these patents and patent application are incorporated herein by reference. For example, a pyrimidine compound (e.g., Compounds 1-27) can be prepared by using 2,4,6-trichloro-pyrimidine as a starting material. The three chloro groups can be displaced by various substitutes. More specifically, first chloro group (e.g., at position 6) can react with, e.g., morpholine, to form a morpholinyl pyrimidine. 2-Aryl and 2-alkylpyrimidinde dichloro compounds can also be prepared by reacting an amidine with a malonic ester followed by treatment with phosphorous oxychloride. Second chloro group can be replaced by reacting with a nucleophile, such as an alcohol in the presence of base, e.g., sodium hydride. In other examples, a compound of formula (I), wherein Y is $CH_2$ (e.g., Compound 1, 3-5, 11, 14, and 27), can be prepared by reacting the pyrimidine chloride with a Grignard reagent, an organotin reagent, an organocopper reagent, an organoboric acid, or an organozinc reagent in the presence of an organopalladium compound as a catalyst. Isomeric forms may be produced. The desired isomeric product can be separated from others by, e.g., high performance liquid chromatography. Third chloro group undergoes a displacement reaction with, e.g., hydrazine, and the primary amine of the coupled hydrazine moiety further reacts with an aldehyde, e.g., indole-3-carboxaldehyde to form a hydrazone linkage. Thus, a pyrimidine compound of this invention is obtained. If preferred, other types of linkages can be prepared by similar reactions. Sensitive moieties on a pyrimidinyl intermediate and a nucleophile can be protected prior to coupling. For suitable protecting groups, see, e.g., Greene (1981) *Protective Groups in Organic Synthesis*, John Wiley & Sons, Inc., New York, the entire teachings of which are incorporated herein by reference. A pyrimidine compound of this invention can be further purified by flash column chromatography, high performance liquid chromatography, or crystallization.

The compounds and compositions described herein are useful to treat and prevent any inflammatory and immune disorders. In particular, the compounds of the invention are useful in inhibiting the production of IL-12, IL-23 and/or IL-27. IL-12 and IL-27 produce INF-γ which further augments the production of IL-12 and causes the differentiation of naïve T cells into $T_H1$ lymphocytes which have been implicated in the pathogenic processes of many autoimmune and inflammatory disorders. IL-23 has been shown to stimulate the differentiation of activated CD4⁺ T cells into $Th_{IL-17}$ cells which produce IL-17, another cytokine that has been implicated in the pathogenic processes of many autoimmune and inflammatory disorders. Thus, in one aspect, the present invention provides a method of treating or preventing autoimmune or inflammatory disorders by inhibiting the production of IL-12, IL-27 and/or IL-23 in a subject by administering to the subject in need thereof an effective amount of a compound of any of the formulae herein, or a pharmaceutically acceptable salt, solvate, clathrate, hydrate, polymorph, or prodrug thereof.

Without wishing to be bound by any theory, since one of the functions of IL-12 and IL-27 is induction of INF-γ expression from T and NK cells which promotes the development of Th1 T lymphocyte type, the compounds of the invention can be used to inhibit the differentiation of naïve T cells into Th1 lymphocytes and/or inhibit the proliferation of Th1 cells. Therefore, in another aspect, the invention features a method of inhibiting the proliferation and/or development of Th1 cells in a subject in need thereof by administering to the subject an effective amount of a compound of any of the formulae herein, or a pharmaceutically acceptable salt, solvate, clathrate, hydrate, polymorph, or prodrug thereof.

Without wishing to be bound by any theory, since one of the functions of IL-23 is to promote the differentiation of activated CD4$^+$ T cells to Th$_{IL-17}$ lymphocyte type which produces the pro-inflammatory cytokine IL-17, the compounds of the invention can be used to inhibit the differentiation of activated CD4$^+$ T cells into Th$_{IL-17}$ lymphocytes and/or inhibit the proliferation of Th$_{IL-17}$ lymphocytes. Therefore, in another aspect, the invention features a method of inhibiting the proliferation and/or development of Th$_{IL-17}$ lymphocytes in a subject in need thereof by administering to the subject an effective amount of a compound of any of the formulae herein, or a pharmaceutically acceptable salt, solvate, clathrate, hydrate, polymorph, or prodrug thereof.

The term "inflammatory disorders" includes any inflammatory disease, disorder or condition caused, exasperated or mediated by IL-12, IL-23, IL-27 and/or IL-17 production. Such inflammatory disorders may include, without limitation, asthma, adult respiratory distress syndrome, systemic lupus erythematosus, inflammatory bowel disease (including Crohn's disease and ulcerative colitis), multiple sclerosis, insulin-dependent diabetes mellitus, autoimmune arthritis (including rheumatoid arthritis, juvenile rheumatoid arthritis, psoriatic arthritis), inflammatory pulmonary syndrome, pemphigus vulgaris, idiopathic thrombocytopenic purpura, autoimmune meningitis, myasthenia gravis, autoimmune thyroiditis, dermatitis (including atopic dermatitis and eczematous dermatitis), psoriasis, Sjogren's Syndrome (including keratoconjunctivitis sicca secondary to Sjogren's Syndrome), alopecia areata, allergic responses due to arthropod bite reactions, aphthous ulcer, iritis, conjunctivitis, keratoconjunctivitis, cutaneous lupus erythematosus, scleroderma, vaginitis, proctitis, drug eruptions (such as Stevens-Johnson syndrome), leprosy reversal reactions, erythema nodosum leprosum, autoimmune uveitis, allergic encephalomyelitis, aplastic anemia, pure red cell anemia, idiopathic thrombocytopenia, polychondritis, Wegener's granulomatosis, chronic active hepatitis, Graves ophthalmopathy, primary biliary cirrhosis, uveitis posterior and interstitial lung fibrosis.

"Inflammatory disorders" expressly include acute inflammatory disorders. Examples of acute inflammatory disorders include graft versus host disease, transplant rejection, septic shock, endotoxemia, Lyme arthritis, infectious meningitis (e.g., viral, bacterial, Lyme disease-associated), an acute episode of asthma and acute episodes of an immune disease.

"Inflammatory disorders" expressly include chronic inflammatory disorders. Nonlimiting examples of chronic inflammatory disorder include asthma, rubella arthritis, and chronic autoimmune diseases, such as systemic lupus erythematosus, psoriasis, inflammatory bowel disease, including Crohn's disease and ulcerative colitis, multiple sclerosis and rheumatoid arthritis.

The term "immune disorders" or "autoimmune disorders" includes any immune disease, disorder or condition caused, exasperated or mediated by IL-12, IL-23 and/or IL-27 production. Such immune diseases may include, without limitation, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosus, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The compounds and compositions described herein are useful to treat and prevent inflammatory disorders and immune disorders. The method involves administering an effective amount of a compound of the invention, or a pharmaceutically acceptable salt, solvate, clathrate, hydrate, polymorph, or prodrug thereof, to a subject in need of treatment for an inflammatory or autoimmune disorder. In preferred embodiments, treatment according to the invention provides a reduction in or prevention of at least one symptom or manifestation of an IL-12-, IL-23-, IL-27, or IL-17-related disorder (e.g., inflammatory disorder or immune diseases), as determined in vivo or in vitro of at least about 10%, more preferably 20%, 30%, 40%, 50%, 60%, 70%, 80%, 90%, 95%, 98% or 99%.

As used herein, the term "effective amount" refers to an amount of a compound of this invention which is sufficient to reduce or ameliorate the severity, duration, progression, or onset of an inflammatory disorder or immune disorder, or one or more symptom thereof, prevent the advancement of an inflammatory disorder or immune disorder, cause the regression of an inflammatory disorder or immune disorder, prevent the recurrence, development, onset or progression of a symptom associated with an inflammatory disorder or immune disorder, or enhance or improve the prophylactic or therapeutic effect(s) of another therapy. An effective amount of the pyrimidine compound of this invention can range from about 0.001 mg/Kg to about 1000 mg/Kg. Effective doses will also vary, as recognized by those skilled in the art, depending on the disorder treated, route of administration, excipient usage, the age and sex of the subject, and the possibility of co-usage with other therapeutic treatments such as use of other agents.

Also within the scope of this invention is a pharmaceutical composition that contains one or more pyrimidine compounds of this invention and a pharmaceutically acceptable carrier.

To practice the method of the present invention, a pyrimidine compound, as a component of a pharmaceutical composition, can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A pyridine compound of this invention can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the compounds of this invention, or one or more solubilizing agents, can be utilized as pharmaceutical excipients for delivery of the pyrimidine compounds. Examples of other carriers include colloidal silicon dioxide, magnesium stearate, cellulose, sodium lauryl sulfate, and D&C Yellow # 10.

The biological activities of a pyrimidine compound can be evaluated by a number of cell-based assays. One of such assays can be conducted using cells from human peripheral blood mononuclear cells (PBMC) or human monocytic cell line (THP-1). The cells are stimulated with a combination of human interferon-γ (IFNγ) and lipopolysaccharide or a combination of IFNγ and *Staphylococcus aureus* Cowan I (SAC) in the presence of a test compound. The level of inhibition of IL-12 production can be measured by determining the amount of p70 by using a sandwich ELISA assay with anti-human IL-12 antibodies. $IC_{50}$ of the test compound can then be determined. Specifically, PBMC or THP-1 cells are incubated with the test compound. Cell viability is assessed using the bioreduction of MTS [3-(4,5-dimethylthiazol-2-yl)-5-(3-carboxymethoxyphenyl)-2-(4-sulfophenyl)-2H-tetrazolium] (Promega, Madison, Wis.).

The level of inhibition of IL-23 inhibition by a compound of the invention can be measured by a similar assay in which human peripheral blood mononuclear cells (PBMC) or human monocytic cell line (THP-1) are stimulated with a combination of human interferon-γ (IFNγ) and lipopolysaccharide (LPS) or a combination of IFNγ and *Staphylococcus aureus* Cowan I (SAC) in the presence of a test compound. The level of inhibition of IL-23 production can be measured by determining the amount of p19 by using a sandwich ELISA assay with antibodies the recognize p19 subunit of IL-23. $IC_{50}$ of the test compound can then be determined. One such assay is disclosed herein in Example 30.

The following specific embodiments are to be construed as merely illustrative, and not limitative of the remainder of the disclosure in any way whatsoever. All of the patents, patent applications, and publications cited herein are hereby incorporated by reference in their entirety.

EXAMPLE 1

Preparation of Compound 1: N-{2-[3-(3,4-dimethoxy-phenyl)-propyl]-6-morpholin-4-yl-pyrimidin-4-yl}-N'-(1H-indol-3-ylmethylene)-hydrazine To a solution of 3-(3,4-dimethoxyphenyl)-propyl iodide (1.224 g, 4.0 mmol) in 20 mL dry THF, highly active zinc (suspension in THF, Rieke metal from Aldrich, 5.2 mL 0.05 g/mL, 4.0 mmol) was added to obtain a mixture. The mixture was stirred at room temperature overnight. 2,4-dichloro-6-morpholinopyrimidine (0.932 g, 4.0 mmol) and trans-benzyl-(chloro)-bis-(triphenylphosphine)palladium(II) (0.03 g, 0.04 mmol) were added to the mixture, and stirred at 60° C. for 2 days. After routine workup, 4-chloro-2-[3-(3,4-dimethoxyphenyl)propyl]-6-morpholinopyrimidine (0.34 g, 0.90 mmol, 22.4%) was separated from 2-chloro-4-[3-(3,4-dimethoxyphenyl)propyl]-6-morpholinopyrimidine (0.45 g, 1.19 mmol, 30%) by flash chromatography purification.

$^1$H NMR (300 MHz, CDCl$_3$), δ (ppm): 6.70-6.80 (m, 3H); 6.32 (s, 1H); 3.87 (s, 3H); 3.85 (s, 3H); 3.73-3.78 (m, 4H); 3.60-3.64 (m, 4H); 2.76 (d, J=7.8 Hz, 2H); 2.63 (d, J=7.5 Hz, 2H); and 2.01-2.12 (m, 2H).

MS (ESI): m/z 380.2 (M+H).

Further, 4-chloro-2-[3-(3,4-dimethoxyphenyl)propyl]-6-morpholinopyrimidine (0.34 g, 0.90 mmol) was reacted with hydrazine (0.29 g, 9 mmol) to obtain 2-[3-(3,4-dimethoxyphenyl)propyl]-4-hydrazino-6-morpholinopyrimidine as a white solid (0.30 g, 0.80 mmol, 89%).

$^1$H NMR (300 MHz, CDCl$_3$), δ (ppm): 6.73-6.80 (m, 3H); 5.88 (s, 1H); 5.74 (s, 1H); 3.87 (s, 3H); 3.85 (s, 3H); 3.76-3.79 (m, 4H); 3.69 (d, J=0.6 Hz, 2H); 3.56-3.60 (m, 4H); 2.64 (d, J=7.5 Hz, 4H); and 2.00-2.15 (m, 2H).

MS (ESI): m/z 374.2 (M−H).

A 5 mL methanol solution containing 2-[3-(3,4-dimethoxyphenyl)-propyl]-4-hydrazino-6-morpholinopyrimidine (0.177 g, 0.50 mmol), indole-3-carboxaldehyde (0.073 g, 0.50 mmol), and AcOH (20 mg, cat.) was stirred at 70° C. for 4 hours. Solvent was removed and the crude residue was purified using flash chromatography to give Compound 1 as a light brown solid (0.21 g, 0.42 mmol, 84%).

$^1$H NMR (300 MHz, CDCl$_3$), δ (ppm): 8.57 (br s, 1H); 8.45 (br s, 1H); 8.29-8.32 (m, 1H); 8.00 (s, 1H); 7.39-7.43 (m, 2H); 7.23-7.34 (m, 2H); 6.74-6.80 (m, 3H); 6.30 (s, 1H); 3.86 (s, 3H); 3.85 (s, 3H); 3.78-3.84 (m, 4H); 3.67-3.70 (m, 4H); 2.63-2.71 (m, 4H), and 2.03-2.13 (m, 2H).

MS (ESI): m/z 501.2 (M+H).

EXAMPLE 2

Preparation of Compound 2: N-(2-n-butoxy-6-morpholin-4-yl-pyrimidin-4-yl)-N'-(1H-indol-3-ylmethylene)-hydrazine To a solution of 2,4,6-trichloro pyrimidine (25 g, 136 mmol) in CH$_2$Cl$_2$ (500 mL) at −78° C., morpholine (11.89 mL, 136 mmol) was slowly added, followed by DIPEA (25 mL, 143 mmol). The obtained reaction mixture was stirred at −78° C. for 5 h, and then warmed up to room temperature. The reaction mixture was washed with water. The obtained organic phase was dried over Na$_2$SO$_4$. The solvent was removed under reduced pressure. The crued residue, 2,4-Dichloro-6-(morpholin-4-yl)pyrimidine, was recrystallized from EtOAc to give white crystals (24.7 g, 77%) 15 g.

$^1$H NMR (300 MHz, CDCl$_3$), δ (ppm): 6.40 (s, 1H); and 4.0-3.5 (m, 8H).

MS (ESI): m/z 234.0 (M+H).

To a solution of n-butanol (0.633 g, 8.54 mmol) in anhydrous DMF (50 mL) at 0° C. under the N$_2$, NaH (0.307 g, 12.8 mmol) was added quickly. The obtained suspension was stirred for 0.5 h at 0° C. 2,4-Dichloro-6-(morpholin-4-yl) pyrimidine (2 g, 8.54 mmol) was added to the suspension. After the suspension was warmed to room temperature and stirred for 12 h, the reaction mixture was quenched with ice/brine and extracted with 200 mL EtOAc. The extract was washed with brine, and dried over Na$_2$SO$_4$. The solvent was removed under reduced pressure. The crude residue was purified using flash chromatography (silica; EtOAc/Hexane: 1/6) to yield 1.4 g of 2-n-butoxy-4-chloro-6-(morpholin-4-yl)pyrimidine (white solid, 60%).

$^1$H NMR (300 MHz, CDCl$_3$), δ (ppm): 6.20 (s, 1H); 4.26 (t, J=6.6 Hz, 2H); 3.78-3.70 (m, 4H); 3.66-3.56 (m, 4H); 1.80-1.68 (m, 2H); 1.54-1.40 (m, 2H); and 0.96 (t, J=6.9, 3H).

MS (ESI): m/z 272.1 (M+H).

To a solution of 2-n-butoxy-4-chloro-6-(morpholin-4-yl) pyrimidine (1.38 g, 5.1 mmol) in dioxane (50 ml), anhydrous hydrazine (1.6 mL, 50 mmol) was added. The obtained reaction mixture was heated to 95° C., and stirred for 12 h under N$_2$. After cooling to room temperature, the reaction mixture was quenched with ice-brine and extracted with EtOAc (200 mL). The organic extract was washed with brine, water, and dried over Na$_2$SO$_4$. The solvent was removed under reduced pressure. The crude residue was recrystallized from methanol to obtain 2-n-butoxy-4-hydrazino-6-(morpholin-4-yl)pyrimidine as white crystals (1.10 g, 81%).

$^1$H NMR (300 MHz, CDCl$_3$), δ (ppm): 5.89 (br s, 1H), 5.49 (s, 1H), 4.26 (t, J=6.6, 2H), 3.84-3.78 (m, 6H), 3.62-3.47 (m, 4H), 1.82-1.67 (m, 2H), 1.55-1.42 (m, 2H), and 0.96 (t, J=6.9, 3H);

MS (ESI): m/z 268.2 (M+H).

To a solution of 2-n-butoxy-4-hydrazino-6-(morpholin-4-yl)pyrimidine (200 mg, 0.748 mmol) in MeOH (20 mL), indole-3-carboxaldehyde (108.6 mg, 0.748 mmol) and acetic acid (a drop) were added sequentially. The obtained reaction mixture was stirred at room temperature for 12 h. White precipitate was formed, collected, and washed with 2 mL methanol to give 200 g of Compound 2 (68%).

$^1$H NMR (300 MHz, CDCl$_3$), δ (ppm): 8.36 (br s, 1H), 8.30 (dd, J=6.6, 1.8, 1H), 8.05 (s, 1H), 8.00 (s, 1H), 7.44-7.40 (m, 2H), 7.33-7.24 (m, 2H), 6.13 (s, 1H), 4.26 (t, 2H, J=6.6), 3.84-3.78 (m, 4H), 3.70-3.64 (m, 4H), 1.80-1.70 (m, 2H), 1.54-1.42 (m, 2H), and 0.96 (t, J=6.9, 3H);

MS (ESI): m/z 395.2 (M+H).

EXAMPLE 3

Preparation of Compound 3: N-(2-(4-hydroxybutyl)-6-morpholin-4-yl-pyrimidin-4-yl)-N'-(1H-indol-3-ylmethylene)-hydrazine A mixture of 4-ethoxy-4-oxo-butylzinc bromide (50 mL 0.5M in THF, 25 mmol), 2,4-dichloro-6-morpholinopyrimidine (4.68 g, 20.0 mmol) and trans-benzyl(chloro)bis(triphenylphosphine)palladium(II) (0.15 g, 0.2 mmol) in THF (total volume 80 mL) was stirred at 60° C. for 2 days. After routine workup, flash chromatography purification was performed to obtain 4-chloro-2-(4-ethoxy-4-oxo-butyl)-6-morpholinopyrimidine as a white solid (2.073 g, 6.60 mmol, 33.0%).

To a solution of 4-chloro-2-(4-ethoxy-4-oxo-butyl)-6-morpholinopyrimidine (1.108 g, 3.54 mmol) in 50 mL THF at −78° C., a diisobutylaluminum hydride (DIBAL) solution (4.72 mL 1.5 M in Toluene, 7.08 mmol) was slowly added. After addition, the obtained reaction mixture was warmed up slowly to 0° C. and kept at 0° C. for 10 min. After routine workup, flash chromatography was performed to obtain 4-chloro-2-(4-hydroxybutyl)-6-morpholinopyrimidine (0.76 g, 2.80 mmol, 79%) as light yellow solid.

$^1$H NMR (300 MHz, CDCl$_3$), δ (ppm): 6.33 (s, 1H), 3.76-3.79 (m, 4H); 3.61-3.68 (m, 6H); 2.76 (t, J=7.8 Hz, 2H); 1.81-1.91 (m, 2H); and 1.60-1.74 (m, 3H).

MS (ESI): m/z 370.2 (M+H).

Following the typical procedure, 4-chloro-2-(4-hydroxybutyl)-6-morpholinopyrimidine (0.542 g, 2.00 mmol, 1.00 equiv.) was reacted with hydrazine and indole-3-carboxaldehyde to give Compound 3 as an off-white solid (0.75 g, 1.90 mmol, 95%).

$^1$H NMR (300 MHz, DMSO-d$_6$), δ (ppm): 11.47 (s, 1H); 10.64 (s, 1H); 8.25 (s, 1H); 8.18 (d, J=6.6 Hz, 1H); 7.71 (s, 1H); 7.43 (d, J=8.4 Hz, 1H); 7.17-7.20 (m, 2H); 6.16 (s, 1H); 4.37 (t, J=4.8 Hz, 1H); 3.72 (br s, 4H); 3.55 (br s, 4H); 3.41-3.45 (m, 2H); 2.49-2.54 (m, 2H), 1.66-1.76 (m 2H); and 1.42-1.53 (m 2H).

MS (ESI): m/z 395.1 (M+H).

EXAMPLE 4

Preparation of Compound 4: N-[2-(2-[1,3]dioxan-2-yl-ethyl)-6-morpholin-4-yl-pyrimidin-4-yl]-N'-(1H-indol-3-ylmethylene)-hydrazine Compound 4 was prepared in a similar manner as described in Example 1.

$^1$H NMR (300 MHz, DMSO-d$_6$), δ (ppm): 11.46 (s, 1H); 10.64 (s, 1H); 8.25 (s, 1H); 8.18 (d, J=6.6 Hz, 1H); 7.71 (s, 1H); 7.43 (d, J=6.0 Hz, 7.5 Hz, 1H); 7.16-7.19 (m, 2H); 6.15 (s, 1H), 4.58 (t, J=5.1 Hz, 1H); 4.00 (dd, J=11.4 Hz, 4.5 Hz, 2H); 3.64-3.72 (m, 6H); 3.54 (br s, 4H); 2.50-2.59 (m, 2H); 1.80-1.94 (m, 3H), and 1.33 (d, J=9.6 Hz, 1H).

MS (ESI): m/z 437.2 (M+H).

EXAMPLE 5

Preparation of Compound 5: N-(1H-indol-3-ylmethylene)-N'-[2-(3-methoxy-propyl)-6-morpholin-4-yl-pyrimidin-4-yl]-hydrazine Following the procedure for the synthesis of N-(2-(4-Hydroxybutyl)-6-morpholin-4-yl-pyrimidin-4-yl)-N'-(1H-indol-3-ylmethylene)-hydrazine (Compound 3), 4-chloro-2-(3-hydroxypropyl)-6-morpholinopyrimidine (0.81 g, 3.15 mmol) was synthesized, methylated with sodium hydride (0.48 g, 6.30 mmol) for 10 min, and MeI (0.895 g, 6.30 mmol) for 5 h in 30 mL THF at 0° C. to give 4-chloro-2-(3-methoxypropyl)-6-morpholinopyrimidine as colorless viscous oil (0.792 g, 3.03 mmol, 96%).

$^1$H NMR (300 MHz, CDCl$_3$), δ (ppm): 6.32 (s, 1H), 3.75-3.79 (m, 4H); 3.61-3.64 (m, 4H); 3.44 (t, J=6.6 Hz, 2H); 3.34 (s, 3H); 2.78 (t, J=7.8 Hz, 2H); and 2.00-2.09 (m, 2H).

MS (ESI): m/z 262.1 (M+H).

Following the typical procedure, 4-chloro-2-(3-methoxypropyl)-6-morpholinopyrimidine (0.783 g, 3.00 mmol) was treated with hydrazine and indole-3-carboxaldehyde sequentially to yield 0.89 g of Compound 5 (2.26 mmol, 75%).

$^1$H NMR (300 MHz, DMSO-d$_6$), δ (ppm): 11.46 (s, 1H); 10.64 (s, 1H); 8.26 (s, 1H); 8.17-8.20 (m, 1H); 7.72 (d, J=2.4 Hz, 1H); 7.43 (dd, J=6.0 Hz, 2.4 Hz, 1H); 7.15-7.21 (m, 2H); 6.16 (s, 1H), 3.70-3.73 (m, 4H); 3.52-3.56 (m, 4H); 3.37 (t, J=6.9 Hz, 2H); 3.23 (s, 3H); 2.50-2.57 (m, 2H), and 1.88-1.97 (m, 2H).

MS (ESI): m/z 395.2 (M+H).

EXAMPLE 6

Preparation of Compound 6: 3-{4-[N'-(1H-indol-3-ylmethylene)-hydrazino]-6-morpholin-4-yl-pyrimidin-2-ylsulfanyl}-propan-1-ol Compound 6 was prepared in a similar manner as described in Example 2.

$^1$H NMR (300 MHz, DMSO-d$_6$), δ (ppm): 11.48 (s, 1H); 10.68 (s, 1H); 8.26 (s, 1H); 8.15-8.18 (m, 1H); 7.73 (d, J=2.1 Hz, 1H); 7.42-7.44 (m, 1H); 7.16-7.20 (m, 2H); 6.04 (s, 1H), 4.53 (t, J=5.1 Hz, 1H); 3.65-3.71 (m, 4H); 3.48-3.56 (m, 6H); 3.06 (t, J=7.2 Hz, 2H), and 1.76-1.85 (m, 2H).

MS (ESI): m/z 413.1 (M+H).

EXAMPLE 7

Preparation of Compound 7: 3-{2-[N'-(1H-indol-3-ylmethylene)-hydrazino]-6-morpholin-4-yl-pyrimidin-4-ylsulfanyl}-propan-1-ol Compound 7 was prepared in a similar manner as described in Example 2.

$^1$H NMR (300 MHz, DMSO-d$_6$), δ (ppm): 11.34 (s, 1H); 10.48 (s, 1H); 8.45 (d, J=7.8 Hz, 1H); 8.25 (s, 1H); 7.64 (d, J=2.7 Hz, 1H); 7.40 (d, J=8.1 Hz, 1H); 7.05-7.19 (m, 2H); 6.08 (s, 1H), 4.60 (t, J=5.1 Hz, 1H); 3.50-3.68 (m, 10H); 3.20-3.30 (m, 2H); and 1.78-1.86 (m, 2H).

MS (ESI): m/z 413.1 (M+H).

EXAMPLE 8

Preparation of Compound 8: N-[2-(2,2-dimethyl-[1,3]dioxolan-4-ylmethoxy)-6-morpholin-4-yl-pyrimidin-4-yl]-N'-(1H-indol-3-ylmethylene)-hydrazine Compound 8 was prepared in a similar manner as described in Example 2.

$^1$H NMR (300 MHz, CDCl$_3$), δ (ppm): 8.38 (br s, 1H); 8.30 (dd, J=7.2, 1.8, 1H), 8.02 (br s, 1H); 8.00 (s, 1H); 7.44-7.41 (m, 2H); 7.32-7.26 (m, 2H); 6.14 (s, 1H); 4.51-4.42 (m, 2H); 4.22-4.12 (m, 2H); 3.96-3.91 (m, 1H); 3.84-3.79 (m, 4H); 3.70-3.64 (m, 4H); 1.47 (s, 3H); and 1.38 (s, 3H).

MS (ESI): m/z 453.2 (M+H).

EXAMPLE 9

Preparation of Compound 9: N-{2-[2-(3,4-dimethoxy-phenyl)-ethoxy]-6-morpholin-4-yl-pyrimidin-4-yl}-N'-(1H-indol-3-ylmethylene)-hydrazine Compound 9 was prepared in a similar manner as described in Example 2.

$^1$H NMR (300 MHz, CDCl$_3$), δ (ppm): 8.43 (bs, 1H); 8.30 (d, J=7.5 Hz 1H); 8.2 (bs, 1H); 8.02 (d, J=2.7 Hz, 1H); 7.46-7.40 (m, 2H); 7.30-7.26 (m, 2H); 6.82 (d, J=1 Hz, 3H); 4.45 (d, J=3.6 Hz, 1H); 4.45 (t, J=5.2 Hz, 2H); 3.87 (d, J=3.9 Hz, 3H); 3.86 (d, J=3.9 Hz, 3H); 3.81 (s, 4H); 3.67 (s, 4H); and 3.04 (t, J=5.0 Hz, 2H).

MS (ESI): m/z 503.2 (M+H).

EXAMPLE 10

Preparation of Compound 10: N-(1H-indol-3-ylmethylene)-N'-[6-morpholin-4-yl-2-(2-pyridin-2-yl-ethoxy)-pyrimidin-4-yl]-hydrazine Compound 10 was prepared in a similar manner as described in Example 2.

$^1$H NMR (300 MHz, CDCl$_3$), δ (ppm): 9.3 (bs, 1H); 8.66 (s, 1H); 8.55-8.53 (m, 1H); 8.28-8.26 (m, 1H); 8.04 (s, 1H); 7.62-7.57 (m, 1H); 7.41-7.10 (m, 6H); 6.08 (s, 1H); 4.64 (t, J=6.6 Hz, 2H); 3.76 (s, 4H); 3.62 (s, 4H); and 3.26 (t, J=6.6 Hz, 2H).

MS (ESI): m/z 444.2 (M+H).

EXAMPLE 11

Preparation of Compound 11: N-(1H-indol-3-ylmethylene)-N'-[6-morpholin-4-yl-2-(3-pyridin-2-yl-propyl)-pyrimidin-4-yl]-hydrazine Compound 11 was prepared in a similar manner as described in Example 1.

$^1$H NMR (300 MHz, DMSO-d$_6$), δ (ppm): 11.47 (s, 1H); 10.65 (s, 1H); 8.50 (d, J=4.5 Hz, 1H); 8.26 (s, 1H); 8.20-8.18 (m, 1H); 7.72-7.68 (m, 2H); 7.45-7.42 (m, 1H); 7.29-7.18 (m, 4H); 6.17 (s, 1H); 3.73 (s, 4H); 3.5 (s, 4H); 2.79 (t, J=7.5 Hz, 2H); 2-58-2.51 (m, 2H); and 2.18-2.06 (m, 2H).

MS (ESI): m/z 442.2 (M+H).

EXAMPLE 12

Preparation of Compound 12: N-(3-methyl-benzylidene)-N'-[6-morpholin-4-yl-2-(2-pyridin-2-yl-ethoxy)-pyrimidin-4-yl]-hydrazine Compound 12 was prepared in a similar manner as described in Example 2.

$^1$H NMR (300 MHz, CDCl$_3$), Λ (ppm): 8.55-8.48 (m, 2H); 7.71 (s, 1H); 7.65-7.55 (m, 1H); 7.49-7.42 (m, 2H); 7.30-7.15 (m, 4H); 6.08 (s, 1H); 4.64 (t, J=6.6 Hz, 2H); 3.81-3.75 (m, 4H); 3.64-3.61 (m, 4H); 3.25 (t, J=7.0 Hz, 2H); and 2.38 (s, 3H).

MS (ESI): m/z 419.2 (M+H).

EXAMPLE 13

Preparation of Compound 13: N-(3-ethyl-benzylidene)-N'-[6-morpholin-4-yl-2-(2-pyridin-2-yl-ethoxy)-pyrimidin-4-yl]-hydrazine Compound 13 was prepared in a similar manner as described in Example 2.

$^1$H NMR (300 MHz, CDCl$_3$), δ (ppm): 8.58-8.50 (m, 1H); 8.43 (s, 1H); 7.95 (s, 1H); 7.64-7.58 (m, 2H); 7.30-7.25 (m, 1H); 7.18-7.05 (m, 3H); 6.07 (s, 1H); 4.65 (t, J=6.9 Hz, 2H); 3.80-3.76 (m, 4H); 3.64-3.61 (m, 4H); 3.26 (t, J=6.9 Hz, 2H); 2.40 (q, J=7.6 Hz, 2H); and 1.45 (t, J=7.6 Hz, 3H).

MS (ESI): m/z 433.3 (M+H).

EXAMPLE 14

Preparation of Compound 14: N-(3-methyl-benzylidene)-N'-[6-morpholin-4-yl-2-(3-pyridin-2-yl-propyl)-pyrimidin-4-yl]-hydrazine Compound 14 was prepared in a similar manner as described in Example 1.

$^1$H NMR (300 MHz, CDCl$_3$), δ (ppm): 9.6 (bs, 1H); 8.53 (d, J=4.5 Hz, 1H); 7.76 (s, 1H); 7.56 (t, J=6 Hz, 1H); 7.49-7.47 (m, 2H); 7.28 (m, 1H); 7.18-7.06 (m, 3H); 6.26 (s, 1H); 3.81-3.79 (m, 4H); 3.69-3.67 (m, 4H); 2.89 (t, J=7.8 Hz, 2H); 2.71 (t, J=7.5 Hz, 2H); 2.39 (s, 3H); and 2.22 (t, J=7.5 Hz, 2H).

MS (ESI): m/z 417.2 (M+H).

EXAMPLE 15

Preparation of Compound 15: N-[6-morpholin-4-yl-2-(2-pyridin-2-yl-ethoxy)-pyrimidin-4-yl]-N'-(1-m-tolyl-ethylidene)-hydrazine Compound 15 was prepared in a similar manner as described in Example 2.

$^1$H NMR (300 MHz, CDCl$_3$), δ (ppm): 8.56 (bs, 1H), 7.66-7.46 (m, 4H), 7.32-7.26 (m, 2H), 7.16-7.14 (m, 2H), 6.44 (s, 1H), 4.69 (t, J=6.9 Hz, 2H), 3.80-3.77 (m, 4H), 3.63-3.60 (m, 4H), 3.31 (t, J=6.9 Hz, 2H), 2.39 (s, 3H).

MS (ESI): m/z 433.2 (M+H).

EXAMPLE 16

Preparation of Compound 16: N-[1-(1H-indol-3-yl)-ethylidene]-N'-[6-morpholin-4-yl-2-(2-pyridin-2-yl-ethoxy)-pyrimidin-4-yl]-hydrazine Compound 16 was prepared in a similar manner as described in Example 2.

$^1$H NMR (300 MHz, CDCl$_3$), δ (ppm): 9.35 (bs, 1H); 8.54 (dd, J=0.9, 4.2 Hz, 1H); 8.33 (d, J=7.5 Hz, 1H); 7.93 (s, 1H); 7.58 (t, J=7.2 Hz, 1H); 7.36-7.33 (m, 2H); 7.27-7.120 (m, 4H); 6.49 (s, 1H); 4.68 (t, J=7.2 Hz, 2H); 3.76-3.73 (m, 4H); 3.60-3-57 (m, 4H); 3.50 (s, 3H); and 3.33-3.28 (t, J=7.0 Hz, 2H).

MS (ESI): m/z 458.2 (M+H).

EXAMPLE 17

Preparation of Compound 17: 3-Methyl-benzaldehyde O-[6-morpholin-4-yl-2-(2-pyridin-2-yl-ethoxy)-pyrimidin-4-yl]-oxime Compound 17 was prepared in a similar manner as described in Example 2.

$^1$H NMR (300 MHz, CDCl$_3$), δ (ppm): 8.56-8.53 (m, 1H); 8.45 (s, 1H); 7.62-7.50 (m, 3H); 7.38-7.26 (m, 3H); 7.18-7.10 (m, 1H); 6.17 (s, 1H); 4.68 (t, J=6.9 Hz, 2H); 3.80-3.76 (m, 4H); 3.67-3.64 (m, 4H); 3.29 (t, J=6.9 Hz, 2H); and 2.41 (s, 3H).

MS (ESI): m/z 420.1 (M+H).

EXAMPLE 18

Preparation of Compound 18: 1H-indole-3-carbaldehyde O-[6-morpholin-4-yl-2-(2-pyridin-2-yl-ethoxy)-pyrimidin-4-yl]-oxime Compound 18 was prepared in a similar manner as described in Example 2.

$^1$H NMR (300 MHz, DMSO-d$_6$), δ (ppm): 11.82 (bs, 1H); 8.81 (s, 1H); 8.50 (d, J=4.5 Hz, 1H); 8.04 (d, J=6.9 Hz, 1H); 7.93 (s, 1H); 7.72 (t, J=6.9 Hz, 1H); 7.49 (d, J=6.9 Hz, 1H); 7.33 (d, J=7.8 Hz, 1H); 7.30-7.18 (m, 3H); 6.22 (s, 1H); 4.57 (t, J=6.3 Hz, 2H); 3.67 (s, 4H); 3.56 (s, 4H); and 3.15 (t, J=6.3 Hz, 2H).

MS (ESI): m/z 445.2 (M+H).

EXAMPLE 19

Preparation of Compound 19: N-(1H-indol-3-ylmethylene)-N'-{6-morpholin-4-yl-2-[2-(pyridin-3-yloxy)-ethoxy]-pyrimidin-4-yl}-hydrazine Compound 19 was prepared in a similar manner as described in Example 2.

$^1$H NMR: (300 MHz, CDCl$_3$), δ (ppm): 9.20 (br s, 1H); 8.30 (br s, 1H); 8.29 (t, J=3.3 Hz, 1H); 8.18-8.12 (m, 2H); 7.44-7.41 (m, 2H); 7.26-7.18 (m, 5H); 6.08 (s, 1H); 4.66 (t, J=4.8 Hz, 2H); 4.29 (t, J=5.0 Hz, 2H); 3.80-3.76 (m, 4H); and 3.67-3.62 (m, 4H).

MS (ESI): m/z 460.2 (M+H).

EXAMPLE 20

Preparation of Compound 20: N-(3-methyl-benzylidene)-N'-{6-morpholin-4-yl-2-[2-(pyridin-3-yloxy)-ethoxy]-pyrimidin-4-yl}-hydrazine Compound 20 was prepared in a similar manner as described in Example 2.

$^1$H NMR (300 MHz, CDCl$_3$), δ (ppm): 8.55 (s, 1H); 8.34 (br s, 1H); 8.30-8.23 (m, 1H); 7.78 (s, 1H); 7.50-7.47 (m, 2H); 7.32-7.24 (m, 1H); 7.20-7.17 (m, 3H); 6.14 (s, 1H); 4.66 (t, J=5.0 Hz, 2H); 4.35 (t, J=4.8 Hz, 2H); 3.83-3.80 (m, 4H); 3.68-3.65 (m, 4H); and 2.40 (s, 3H).

MS (ESI): m/z 435.2 (M+H).

EXAMPLE 21

Preparation of Compound 21: Butyl-{4-[N'-(1H-indol-3-ylmethylene)-hydrazino]-6-morpholin-4-yl-pyrimidin-2-yl}-amine Compound 21 was prepared in a similar manner as described in Example 2.

$^1$H NMR (300 MHz, CDCl$_3$), δ ppm: 8.41 (bs, 1H), 8.33-8.30 (m, 1H), 8.19 (bs, 1H), 7.95 (s, 1H), 7.41-7.37 (m, 2H), 7.29-7.25 (m, 2H), 5.96 (s, 1H), 4.65 (t, J=4 Hz, 1H), 3.83-3.80 (m, 4H), 3.65-3.62 (m, 4H), 3.36 (dd, J=6.3, 13.5 Hz, 2H), 1.60-1.55 (m, 2H), 1.35-1.33 (m, 4H), 0.92-0.87 (m, 3H).

MS (ESI): m/z 408.2 (M+H).

EXAMPLE 22

Preparation of Compound 22: N-(3-Methyl-benzylidene)-N'-[6-morpholin-4-yl-2-(pyridin-3-yloxy)-pyrimidin-4-yl]-hydrazine To a solution of 3-hydroxypyridine (950 mg, 10 mmol) in anhydrous THF (50 mL) at 0° C. under the nitrogen protection was added NaH (60% in oil) (480 mg, 12 mmol). The suspension was stirred for 0.5 h at 0° C., and 2,4,6-trichloropyrimidine (1.84 g, 10 mmol) was added. After the mixture warmed to room temperature and stirred for 2 h, the reaction was quenched by ice brine and extracted with EtOAc (300 mL). The organic phase was washed with brine, dried (Na$_2$SO$_4$), filtered, evaporated in vacuo. The cure product was purified by flash chromatography on a column of silica gel (EtOAc-Hexane, 1:7). The product (1.80 g, 7.4 mmol) in CH$_2$Cl$_2$ (150 mL) at 0° C. was added slowly morpholine (2.5 g, 28 mmol). The reaction mixture was stirred at 0° C. for 1 h and another 1 h at room temperature. The mixture was washed with water. The organic phase was dried (Na$_2$SO$_4$), filtered and evaporated in vacuo and presented three isomers. The isomers was separated by flash chromatography on a column of silica gel (EtOAc-Hexane, 1:7 and 1:3) to obtain 4-[6-chloro-2-(pyridin-3-yloxy)-pyrimidin-4-yl]-morpholine (320 mg, 14.7%).

$^1$H NMR (300 MHz, CDCl$_3$), δ (ppm): 8.51 (d, 1H, J=2.7 Hz), 8.44 (dd, 1H, J=1.5, J=3.3 Hz), 7.53-7.49 (m, 1H), 7.34-7.3 (m, 1H), 6.25 (s, 1H), 3.71-3.67 (m, 4H), 3.51-3.48 (m, 4H).

MS (ESI): m/z 293.1.

To a solution of 4-[6-chloro-2-(pyridin-3-yloxy)-pyrimidin-4-yl]-morpholine (295 mg, 1 mmol) in THF (10 mL) was added anhydrous hydrazine (0.320 ml, 10 mmol) under the nitrogen protection. The mixture was heated at 70° C. for 15 min. After cooling to room temperature, the reaction mixture was quenched by ice brine and extracted with EtOAc (100 mL). The organic phase was washed with brine (10 mL) and water (10 ml×2), dried (Na$_2$SO$_4$), filtered, evaporated, and purified by flash chromatography on a column of silica gel (CH$_2$Cl$_2$ and CH$_2$Cl$_2$-MeOH, 95:5) and to give [6-morpholin-4-yl-2-(pyridin-3-yloxy)-pyrimidin-4-yl]-hydrazine (180 mg) in 62% yield. M/Z (M+1) 289.2

To a solution of [6-morpholin-4-yl-2-(pyridin-3-yloxy)-pyrimidin-4-yl]-hydrazine (180 mg) (145 mg, 0.5 mmol) and m-tolylaldehyde (72 mg, 0.6 mmol) in MeOH (10 mL) was added acetic acid (1 drop). The reaction mixture was stirred at room temperature for 12 h and white solid was precipitated. The resulting precipitate was collected by filtration and washed with little amount of metanol and to give 125 mg of Compound 22 in 64% yield.

$^1$H NMR (300 MHz, CDCl$_3$), δ (ppm): 8.71 (s, 1H), 8.57 (d, 1H, J=2.4 Hz), 8.44 (dd, 1H, J=1.5, 3.2 Hz), 7.78 (s, 1H), 7.56-7.52 (m, 1H), 7.46-7.43 (m, 2H), 7.34-7.26 (m, 2H), 7.17 (d, 1H, J=8.1 Hz), 6.17 (s, 1H), 3.76-3.73 (m, 4H), 3.57-3.54 (m, 4H), 2.38 (s, 3H).

MS (ESI): m/z 391.2.

EXAMPLE 23

Preparation of Compound 23: N-(3-Methylbenzlidene)-N'-(5-methyl-6-morpholin-4-yl-2-phenylpyrimidin-4-yl)hydrazine Benzamidine hydrochloride (7.06 g, 0.045 mol) and dimethyl methylmalonate (6.0 g, 0.041 mol) were dissolved in methanol (100 mL). Sodium methoxide (21.5 mL, 0.099 mol, 25 wt % solution in methanol) was added and the solution was stirred at room temperature for 18 h. The volume of solvent was redcued to approximately 50 mL under reduced pressure, then poured onto ice water. This solution was neutralized with HOAc which produced a white precipitate. This precipitate was collected and dried to produce a white solid (6.1 g, 74%).

$^1$H NMR (DMSO-d$_6$) δ (ppm) 1.68 (s, 3H), 7.70-7.87 (m, 3H), 8.21 (d, J=8.4 Hz).

MS (ESI): m/z 203.1 (M+H)$^+$

5-Methyl-2-phenyl-pyrimidine-4,6-diol (3.3 g, 0.016 mol) and POCl$_3$ were heated to 60 C for 3 hrs. The solution was allowed to cool to room temperature then poured onto ice. The resultant white precipitate was filtered and dried to produce the desired compound as a white solid (810 mg, 21%).

$^1$H NMR (DMSO-d$_6$) δ (ppm) 2.40 (s, 3H), 7.51-7.56 (m, 3H), 8.23 (d, 8.4 Hz).

MS (ESI): m/z 239.1 (M+H)$^+$ 4,6-Dichloro-5-methyl-2-phenylpyrimidine (2.5 g, 0.010 mol) and morpholine (2.93 g, 0.031 mol) were dissolved in THF (50 mL) and heated to reflux for 3 hrs. The solution was allowed to cool then EtOAc (100 mL) and water (100 mL) were added. The EtOAc layer was washed with water (3×100 mL), dried over MgSO$_4$, filtered and solvent was removed under reduced pressure. The resultant solid was used without further purification (2.66 g, 92%).

MS (ESI): m/z 298.1 (M+H)$^+$ 4-(6-Chloro-5-methyl-2-phenylpyrimidin-4-yl)morpholine (439 mg, 1.51 mmol) was dissolved in THF (50 mL). Hydrazine (0.25 mL, 7.96 mmol) was added and the solution was heated to reflux for 18 hrs. The reaction was allowed to cool the solvent was removed under reduced pressure. EtOAc (100 mL) and water (100 mL) were added. The EtOAc layer was washed with water (3×100 mL), dried over MgSO$_4$, filtered and solvent was removed under reduced pressure to produce a white solid (374 mg). This solid was redissolved in THF (50 mL) and m-tolualdehyde (157 mg, 1.31 mmol) was added. The solution was heated to reflux for 4 hrs then allowed to cool. Solvent was removed under reduced pressure then EtOAc (100 mL) and water (100 mL) were added. The EtOAc layer was washed with water (3×100 mL), dried over MgSO$_4$, filtered and solvent was removed under reduced pressure. The crude product was purified by silcagel column chromatography, eluting with 25% EtOAc/hexane to produce the pure desired product as a yellow solid (313 mg, 53%). $^1$H NMR (DMSO-d$_6$) δ (ppm) 2.26 (s, 3H), 2.36 (s, 3H), 3.35 (m, 4H), 3.75-3.78 (m, 4H), 7.20 (d, J=6.9 Hz), 7.33 (t, J=6.9 Hz), 7.47-7.52 (m, 5H), 8.19 (s, 1H), 8.35-8.38 (m, 2H), 10.60 (s, 1H).

MS (ESI): m/z 388.3 (M+H)$^+$

EXAMPLE 24

Preparation of Compound 24: N-(3-methyl-benzylidene)-N'-(2-phenyl-6-thiomorpholin-4-yl-pyrimidin-4-yl)-hydrazine Compound 24 was prepared in a similar manner as described in Example 23.

$^1$H-NMR (DMSO-d$_6$) δ 2.36 (s, 3H), 2.76 (s, 4H), 4.07 (s, 4H), 6.36 (s, 1H), 7.19 (d, J=8.1 Hz), 7.32 (t, J=8.1 Hz), 7.47-7.57 (m, 5H), 8.09 (s, 1H), 8.30-8.31 (m, 1H), 11.02 (s, 1H).

MS (ESI): m/z 389.1.

EXAMPLE 25

Preparation of Compound 25: (2,3-Dimethyl-1H-indole-5-yl)-{6-morpholin-4-yl-2-[2-(pyridin-3-yloxy)-ethoxy]-pyrimidin-4-yl}-amine To a solution of 2-(pyridin-3-yloxy)-ethanol (3.48 g, 25 mmol) in 40 mL of anhydrous THF at room temperature under the N$_2$,2,4,6-trichloro pyrimidine (4.56 g, 25 mmol) was added followed by portionwise addition of NaH (60% suspension in oil, 1.1 g, 27.5 mmol). After 30 min of stirring reaction was quenched with water, water layer extracted with EtOAc, combined organic solutions washed with brine and dried over MgSO$_4$.

Purification using flash chromatography (silica; dichloromethane/acetone/methanol: 3/1/0.1) afforded mixture of 4,6-dichloro-2- and 2,6-dichloro-4-[2-(pyridin-3-yloxy)-ethoxy]-pyrimidines (3.72 g, 52%), (NMR ratio 1:1.2) as an oil.

To a solution of the above mixture (3.72 g, 13 mmol) in 20 mL of 1,4-dioxane was added DIPEA (2.49 mL, 14.3 mmol), followed by 2,3-dimethyl-5-amino-indole (2.08 g, 13 mmol) and a mixture was refluxed for 1 hour. Solvent was removed under reduced pressure and reaction mixture was separated using column chromatography (silica; dichloromethane/acetone/methanol: 3/1/0.1) to afford {6-chloro-2-[2-(pyridin-3-yloxy)-ethoxy]-pyrimidin-4-yl}-amine (2.07 g, 39%). An mixture of {4-chloro-6-[2-(pyridin-3-yloxy)-ethoxy]-pyrimidin-4-yl}-amine and {2-chloro-6-[2-(pyridin-3-yloxy)-ethoxy]-pyrimidin-4-yl}-amine (2.5 g, 47%) was also obtained and used in another reaction.

A solution of {6-chloro-2-[2-(pyridin-3-yloxy)-ethoxy]-pyrimidin-4-yl}-amine (2.07 g, 5.05 mmol) and morpholine (1.32 mL, 15.15 mmol) in 1,4-dioxane was heated at 110° C. for 24 hours. Solvent was removed under reduced pressure and reaction mixture was purified using flash chromatography (silica; dichloromethane/acetone/methanol: 3/1/0.1) to afford Compound 25 (2 g, 86%) as a colorless solid.

$^1$H NMR (300 MHz, CDCl$_3$), δ (ppm): 8.34 (br s, 1H), 8.23 (dd, 1H, J=3.6, 2.1), 7.96 (brs, 1H), 7.34-7.21 (m, 4H), 6.98 (dd, 1H, J=8.4, 1.8 Hz), 6.60 (brs, 1H), 5.36 (s, 1H), 4.65 (t, 2H, J=5.1 Hz), 4.34 (t, 2H, J=5.1 Hz), 3.66 (m, 4H), 3.42 (m, 4H), 2.37 (s, 3H), and 2.20 (s, 3H).

MS (ESI): m/z 461.5 (M+H).

EXAMPLE 26

Preparation of Compound 26: (2,3-Dimethyl-1H-indole-5-yl)-{4-morpholin-4-yl-6-[2-(pyridin-3-yloxy)-ethoxy]-pyrimidin-2-yl}-amine Reaction of a mixture of {4-chloro-6-[2-(pyridin-3-yloxy)-ethoxy]-pyrimidin-4-yl}-amine and {2-chloro-6-[2-(pyridin-3-yloxy)-ethoxy]-pyrimidin-4-yl}-amine (2.5 g, 47%) and (2.5 g, 6.1 mmol) with morpholine was carried out as described in Example 24.

Purification by flash chromatography and recrystallization from ether-pentane gave 0.3 g of Compound 26.

$^1$H NMR (300 MHz, CDCl$_3$), δ (ppm): 8.36 (br s, 1H), 8.24 (m, 1H), 7.85 (m, 1H), 7.70 (brs, 1H), 7.26-7.14 (m, 4H), 6.78 (brs, 1H), 5.42 (s, 1H), 4.68 (t, 2H, J=5.1), 4.31 (t, 2H, J=5.1), 3.70 (m, 4H), 3.54 (m, 4H), 2.35 (s, 3H), and 2.18 (s, 3H).

MS (ESI): m/z 461.5 (M+H).

EXAMPLE 27

Preparation of Compound 27: 3-{4-[N'-(3-Methylbenzylidene)-hydrazino]-6-morpholin-4-yl-pyrimidin-2-yl}-propionic acid ethyl ester Compound 27 was prepared in a similar manner as described in Example 1.

$^1$H NMR (300 MHz, CDCl$_3$), δ (ppm): 8.22 (s, 1H); 7.69 (s, 1H); 8.07 (s, 1H); 7.47 (m, 2H); 7.28 (t, J=7.5 Hz, 1H); 7.17 (d, J=7.5 Hz, 1H); 6.23 (s, 1H); 4.13 (q, J=7.2 Hz, 2H); 3.78-3.81 (m, 4H); 3.62-3.65 (m, 4H); 2.98 (t, J=7.2 Hz, 2H); 2.77 (t, J=7.2 Hz, 2H); 2.39 (s, 3H); 1.24 (t, J=7.2 Hz, 3H).

MS (ESI): m/z 398.2 (M+H).

EXAMPLE 28

In Vitro Assays

Reagents. *Staphylococcus aureus* Cowan I (SAC) was obtained from Calbiochem (La Jolla, Calif.), and lipopolysaccharide (LPS, *Serratia marscencens*) was obtained from Sigma (St. Louis, Mo.). Human and mouse recombinant IFNγ were purchased from Boehringer Mannheim (Mannheim, Germany) and Pharmingen (San Diego, Calif.), respectively.

Human In Vitro Assay. Human PBMC were isolated by centrifugation using Ficoll-Paque (Pharmacia Biotech, Uppsala, Sweden) and prepared in RPMI medium supplemented with 10% fetal calf serum (FCS), 100 U/mL penicillin, and 100 μg/mL streptomycin. PBMC were plated in wells of a 96-well plate at a concentration of 5×10$^5$ cells/well, and primed by adding IFNγ (30 U/mL) for 22 h and stimulated by adding LPS (1 μg/mL), or by adding IFNγ (100 U/mL) and then stimulated by adding SAC (0.01%). A test pyrimidine compound was dissolved in DMSO, and added to wells of the 96-well plate. The final DMSO concentration was adjusted to 0.25% in all cultures, including the compound-free control. Human THP-1 cells were plated in wells, primed by adding IFNγ (100 U/mL) for 22 h and stimulated by adding SAC (0.025%) in the presence of different concentrations of the pyrimidine compound. Cell-free supernatants were taken 18 h later for measurement of cytokines. Cell viability was assessed using the bioreduction of MTS. Cell survival was estimated by determining the ratio of the absorbance in compound-treated groups versus compound-free control.

The supernatant was assayed for the amount of IL-12p40, IL-12p70, or IL-10 by using a sandwich ELISA with anti-human antibodies, i.e., a Human IL-12 p40 ELISA kit from R&D Systems (Berkeley, Calif.), and a Human IL-12 p70 or IL-10 ELISA kit from Endogen (Cambridge, Mass.). Assays were based on the manufacturer's instructions.

Murine In Vitro Assay. Balb/c mice (Taconic, Germantown, N.Y.) were immunized with *Mycobacterium tuberculosis* H37Ra (Difco, Detroit, Mich.). The splenocytes were harvested 5 days and prepared in RPMI medium supplemented with 10% FCS and antibiotics in a flat bottom 96-well plate with $1 \times 10^6$ cells/well. The splenocytes were then stimulated with a combination of IFNγ (60 ng/mL) and SAC (0.025%) [or LPS (20 μg/mL)] in the presence of a test compound. Cell-free supernatants were taken 24 h later for the measurement of cytokines. The preparation of compound and the assessment of cell viability were carried out as described above. Mouse IL-12 p70, IL-10, IL-1β, and TNFα were measured using ELISA kits from Endogen, according to the manufacturer's instructions.

The biological activities of pyrimidine compounds were tested on human PBMC or THP-1 cells. Many of the compounds have $IC_{50}$ values of 5 μM or less. Unexpectedly, some of the test compounds have $IC_{50}$ values as low as 1 nM.

EXAMPLE 29

In Vivo Assays

Treatment of adjuvant arthritis in rats: Adjuvant arthritis (AA) was induced in female Lewis rats by the intracutaneous injection (base of the tail) of 0.1 mL of a 10 mg/mL bacterial suspension made from ground, heat-killed *Mycobacterium tuberculosis* H37Ra suspended in incomplete Freund's adjuvant. Rats were given a test compound orally once a day for 12 days, starting the day following the induction. The development of polyarthritis was monitored daily by macroscopic inspection and assignment of an arthritis index to each animal, during the critical period (days 10 to 25 post-immunization).

The intensity of polyarthritis was scored according to the following scheme: (a) Grade each paw from 0 to 3 based on erythema, swelling, and deformity of the joints: 0 for no erythema or swelling; 0.5 if swelling is detectable in at least one joint; 1 for mild swelling and erythema; 2 for swelling and erythema of both tarsus and carpus; and 3 for ankylosis and bony deformity. Maximum score for all 4 paws was thus 12. (b) Grade for other parts of the body: for each ear, 0.5 for redness and another 0.5 if knots are present; 1 for connective tissue swelling (saddle nose); and 1 for the presence of knots or kinks in the tail. The highest possible arthritic index was 16.

Experiments with the AA model were repeated four times. Oral administration of pyrimidine compounds of this invention (e.g., Compound 12) reproducibly reduced the arthritic score and delayed the development of polyarthritis in a dose-dependent manner. The arthritis score used in this model was a reflection of the inflammatory state of the structures monitored and the results therefore show the ability of the test compound to provide relief for this aspect of the pathology.

Treatment of Crohn's disease in dinitrobenzene sulfonic acid-induced inflammatory bowel syndrome model rats: Wistar derived male or female rats weighing 200±20 g and fasted for 24 hours were used. Distal colitis was induced by intra-colonic instillation of 2,4-dinitrobenzene sulfonic acid (DNBS, 25 mg in 0.5 mL ethanol 30%) after which air (2 mL) was gently injected through the cannula to ensure that the solution remained in the colon. A test compound and/or vehicle was administered orally 24 and 2 hours before DNBS instillation and then daily for 5 days. One control group was similarly treated with vehicle alone while the other is treated with vehicle plus DNBS. The animals were sacrificed 24 hours after the final dose of test compound administration and each colon was removed and weighed. Colon-to-body weight ratio was then calculated for each animal according to the formula: Colon (g)/BW×100. The "Net" increase in ratio of Vehicle-control+DNBS group relative to Vehicle-control group was used as a base for comparison with test substance treated groups and expressed as "% Deduction." Pyrimidine compounds of this invention (e.g., Compound 12) reproducibly had about 30% deduction. A 30% or more reduction in colon-to-body weight ratio, relative to the vehicle treated control group, was considered significant.

Rats treated with test substance orally showed a marked reduction in the inflammatory response. These experiments were repeated three times and the effects were reproducible.

Treatment of Crohn's disease in $CD4^+$ $CD45Rb^{high}$ T cell-reconstituted SCID colitis model mice: Spleen cells were prepared from normal female BALB/c mice. For cell purification, the following anti-mouse antibodies were used to label non-$CD4^+$ T cells: B220 (RA3-6B2), CD11b (M1/70), and CD8α (53-6.72). All antibodies were obtained from BioSource (Camarillo, Calif.). M450 anti-rat IgG-coated magnetic beads (Dynal, Oslo, Norway) were used to bind the antibodies and negative selection was accomplished using an MPC-1 magnetic concentrator. The enriched $CD4^+$ cells were then labeled for cell sorting with FITC-conjugated CD45RB (16A, Pharmingen, San Diego, Calif.) and PE-conjugated CD4 (CT-CD4, Caltag, Burlingame, Calif.). $CD4^+$ $CD45RB^{high}$ cells were operationally defined as the upper 40% of CD45Rb-staining $CD4^+$ cells and sorted under sterile conditions by flow cytometry. Harvested cells were resuspended at $4 \times 10^6$/mL in PBS and injected 100 μL intraperitoneally into female C.B-17 SCID mice. Pyrimidine compounds of this invention (e.g., Compound 12) and/or vehicle was orally administered once a day, 5 days per week, starting the day following the transfer. The transplanted SCID mice were weighed weekly and their clinical condition was monitored.

Colon tissue samples were fixed in 10% buffered formalin and embedded in paraffin. Sections (4 μm) collected from ascending, transverse, and descending colon were cut and stained with hematoxylin and eosin. The severity of colitis was determined based on histological examination of the distal colon sections, whereby the extent of colonic inflammation was graded on a scale of 0-3 in each of four criteria: crypt elongation, cell infiltration, depletion of goblet cells, and the number of crypt abscesses.

LP lymphocytes were isolated from freshly obtained colonic specimens. After removal of payer's patches, the colon was washed in Ca/Mg-free HBSS, cut into 0.5 cm pieces and incubated twice in HBSS containing EDTA (0.75 mM), DTT (1 mM), and antibiotics (amphotericin 2.5 μg/mL, gentamicin 50 μg/mL from Sigma) at 37° C. for 15 min. Next, the tissue was digested further in RPMI containing 0.5 mg/mL collagenase D, 0.01 mg/mL DNase I (Boehringer Manheim), and antibiotics at 37° C. LP cells were then layered on a 40-100% Percoll gradient (Pharmacia, Uppsala, Sweden), and lymphocyte-enriched populations were isolated from the cells at the 40-100% interface.

To measure cytokine production, 48-well plates were coated with 10 μg/mL murine anti-CD3ϵ antibody (145-2C11) in carbonate buffer (PH 9.6) overnight at 4° C. $5 \times 10^5$ LP cells were then cultured in 0.5 ml of complete medium in precoated wells in the presence of 1 μg/mL soluble anti-CD28 antibody (37.51). Purified antibodies were obtained from Pharmingen. Culture supernatants were removed after 48 h and assayed for cytokine production. Murine IFNγ was measured using an ELISA kit from Endogen (Cambridge, Mass.), according to the manufacturer's instructions.

Histological analysis showed that oral administration of pyrimidine compounds of this invention (e.g., Compound 12) reduced colonic inflammation as compared to vehicle control. The suppressive effect was dose-dependent with a substantial reduction at a dose of 10 mg/kg. The calculated colon-to-body weight ratio was consistent with the histological score, showing attenuation by treatment with the test compound. Furthermore, analysis of cytokines from LP cells in response to anti-CD3 antibody and anti-CD28 antibody demonstrated that LP cells from vehicle control produced an augmented level of IFNγ and treatment with test substance greatly diminished the production. These results clearly demonstrated the potential of the test substance in treatment of inflammatory bowel disease represented by Crohn's disease.

EXAMPLE 30

Inhibition of IL-23

Figure 2:
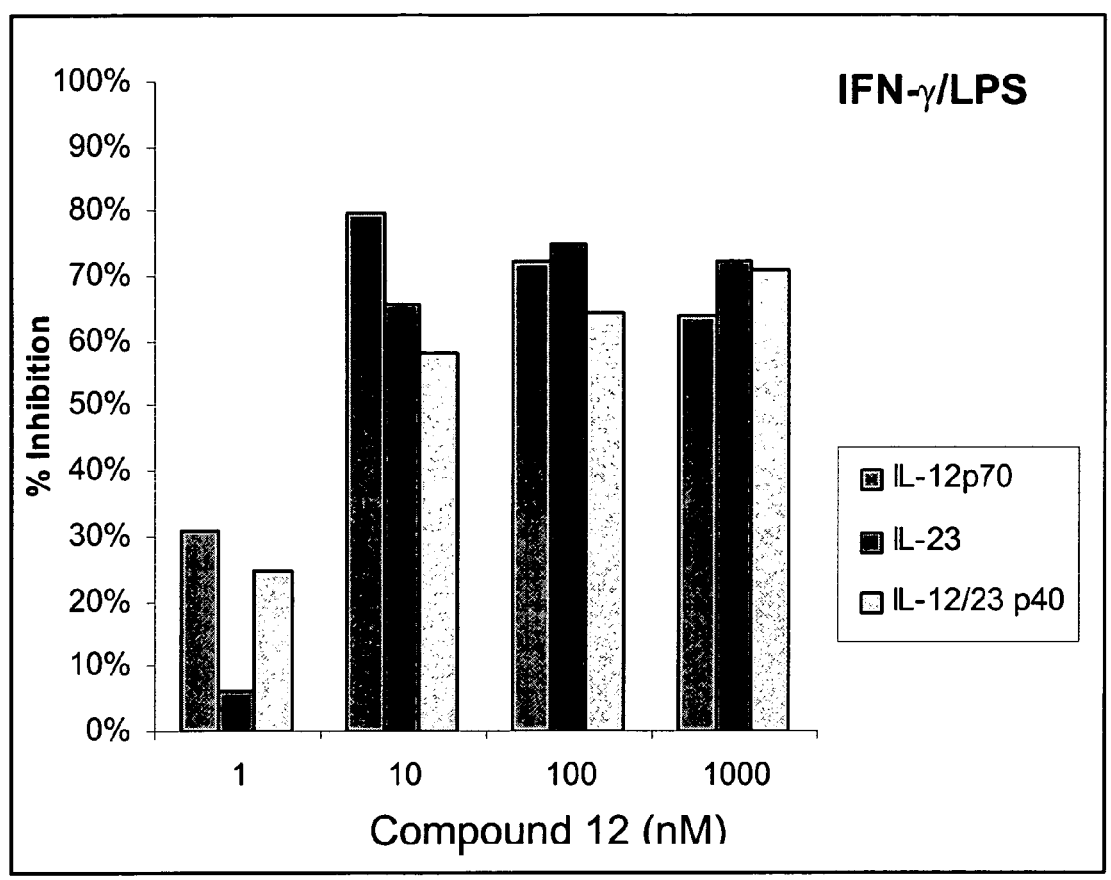
FIG. 2 is a graph showing the percent inhibition of IL-12, IL-23 and the p40 subunit of IL-12 and IL-23 by Compound 12 in human peripheral blood mononuclear cells after stimulation with liposaccharide (LPS) in the presence of IFN-γ.

The compounds of the invention inhibit the expression of p40 that is a subunit of both IL-12 and IL-23. Therefore, inhibition of IL-23 in addition to IL-12 is expected. In order to confirm the hypothesis, an assay was established to specifically detect IL-23 using polyclonal antibodies recognizing p19 (R&D Systems, MN), an IL-23 specific subunit. A 96-well plate was coated with the antibodies at 1 μg/ml, and after washing incubated with the supernatants of human peripheral blood mononuclear cells (PBMC). The culture was stimulated with 1 μg/ml of liposaccharide (LPS) (FIG. 2) or 0.025% of *S. aureus* Cowan I (SAC) (FIG. 1) in the presence of test compound after IFN-γ priming. The captured IL-23 was then detected by a biotinylated goat anti-human p40 antibody that binds to p40 subunit of human IL-12 and IL-23 as a monomer or in the context of the respective heterodimer (Part 840099 of product DY1240 from R&D Systems). The plate was developed by incubation with streptavidin-HRP and then substrate solution (R&D Systems Cat # DY999). Recombinant IL-23 (R&D Systems) was added as standard in the assay. The estimated detection range is from 0.1 to 10 ng/ml, and 1 ng/ml recombinant IL-12 heterodimer (Cell Sciences, MA) and p40 monomer (R&D Systems) were under detection limit. To compare with the inhibition of IL-23, the supernatant was also analyzed for IL-12 heterodimer and total p40 proteins using IL-12 specific ELISA kit (Cell Sciences) and p40 ELISA kit (R&D Systems) respectively. IL-23 was significantly induced in IFN-γ/SAC and IFN-γ/LPS-stimulated human PBMC, and was inhibited by compound 12 in a dose-dependent manner. The inhibitory activity of compound 12 against IL-23 was comparable to that against p40 and slightly lower than that against IL-12.

EXAMPLE 31

Gene Expression of Peripheral Blood Mononuclear Cells After Treatment with a Compound of the Invention Changes in gene expression patterns of peripheral blood mononuclear cells (PBMC) are studied using a gene chip microarrays (Affymetrix, Inc.). PBMC are stimulated with IFNγ plus SAC, then dosed with 0.1, 1.0, 10, 100, or 1000 nM of a compound of the invention for 3 h. Control PBMC are stimulated with IFγ alone and IFNγ plus SAC. Changes in gene expression patterns between the control samples and the samples dosed with a compound of the invention are compared. In order to know the kinetics in the expression, PBMC with IFNγ/SAC are further studied at different time points (20 min, 1.5 h, 3 h, 6 h, and 16 h) after the addition of the stimulus. In addition, PBMC preparations can be fractionated into T-cell enriched and monocyte-macrophage enriched populations, in order to distinguish the effects of a compound of the invention on these cell populations, following IFNγ/SAC stimulation.

Genes preferentially expressed in monocyte/macrophage cells include first and foremost, those encoding the p40 subunit of IL-12 and IL-23, as well as the p35 subunit of IL-12. The expression of EBI3 is induced after stimulation with IFNγ/SAC, and is expected to be dose-dependently inhibited by a compound of the invention because IL-27 is a heterodimer formed from subunits EBI3 and p28, and EBI3 shares 27% amino acid sequence homology with IL-12 p40 and p28 is a protein related to the p35 subunit of IL-12.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous a pyrimidine compound described in the specification also can be made, screened for their inhibiting IL-12 activities, and used to practice this invention. Thus, other embodiments are also within the claims.

What is claimed is:

1. A method of inhibiting IL-23 in vitro comprising administering to a cell a compound of formula (I):

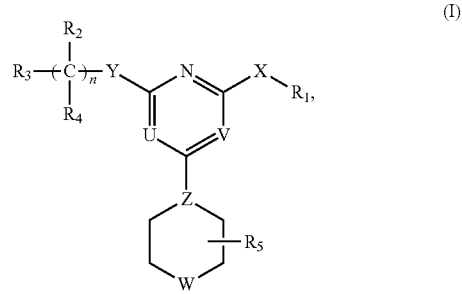

or a pharmaceutically acceptable salt thereof, wherein

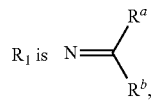

aryl, or heteroaryl;

each of $R_2$ and $R_4$, independently, is $R^c$, halogen, nitro, cyano, isothionitro, $SR^c$, or $OR^c$; or $R_2$ and $R_4$, taken together, is carbonyl;

$R_3$ is $R^c$, alkenyl, alkynyl, $OR^c$, $OC(O)R^c$, $SO_2R^c$, $S(O)R^c$, $S(O_2)NR^cR^d$, $SR^c$, $NR^cR^d$, $NR^cCOR^d$, $NR^cC(O)OR^d$, $NR^cC(O)NR^cR^d$, $NR^cSO_2R^d$, $COR^c$, $C(O)OR^c$, or $C(O)NR^cR^d$;

$R_5$ is H or alkyl;

n is 0, 1, 2, 3, 4, 5, or 6;

X is O, S, S(O), $S(O_2)$, or $NR^c$;

Y is a covalent bond, $CH_2$, C(O), C=N—$R^c$, C=N—$OR^c$, C=N—$SR^c$, O, S, S(O), $S(O_2)$, or $NR^c$;

Z is N or CH;

one of U and V is N, and the other is $CR^c$; and

W is O, S, S(O), $S(O_2)$, $NR^c$, or $NC(O)R^c$;

in which each of $R^a$ and $R^b$, independently, is H, alkyl, aryl, heteroaryl; and each of $R^c$ and $R^d$, independently, is H, alkyl, aryl, heteroaryl, cyclyl, heterocyclyl, or alkylcarbonyl.

2. The method of claim 1, wherein $R_1$ is

3. The method of claim 2, wherein U is N and V is CH.

4. The method of claim 2, wherein Z is N and W is O.

5. The method of claim 2, wherein X is $NR^c$.

6. The method of claim 5, wherein $R^c$ is H, methyl, ethyl, or acetyl.

7. The method of claim 2, wherein Y is O or $CH_2$, and n is 0, 1, 2, 3, or 4.

8. The method of claim 7, wherein $R_3$ is aryl or heteroaryl.

9. The method of claim 8, wherein $R_3$ is pyridinyl.

10. The method of claim 2, wherein one of $R^a$ and $R^b$ is

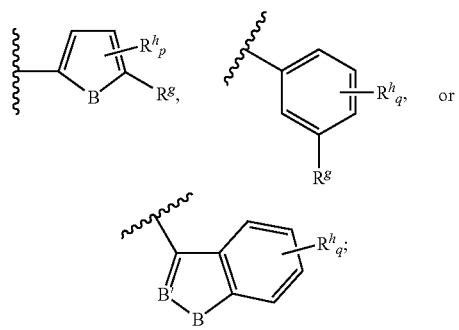

wherein:

B is $NR^i$, O, or S;

B' is N or $CR^i$;

$R^g$ is H, alkyl, or alkoxyl;

$R^h$ is halogen, $NO_2$, CN, alkyl, aryl, heteroaryl, $OR^c$, $OC(O)R^c$, $SO_2R^c$, $S(O)R^c$, $S(O_2)NR^cR^d$, $SR^c$, $NR^cR^d$, $NR^cCOR^d$, $NR^cC(O)OR^d$, $NR^cC(O)NR^cR^d$, $NR^cSO_2R^d$, $COR^c$, $C(O)OR^c$, or $C(O)NR^cR^d$;

$R^i$ is H, alkyl, or alkylcarbonyl;

p is 0, 1, or 2; and q is 0, 1, 2, 3, or 4.

11. The method of claim 10, wherein one of $R^a$ and $R^b$ is

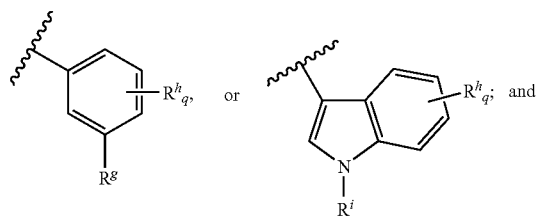

the other of $R^a$ and $R^b$ is H or alkyl.

12. The method of claim 11, wherein $R^g$ is H, methyl, ethyl, propyl, cyclopropyl, methoxy, or ethoxy; $R^h$ is F, Cl, CN, methyl, methoxy, ethoxy, $OC(O)CH_3$, $OC(O)C_2H_5$, $C(O)OH$, $C(O)OC_2H_5$, $C(O)NH_2$, $NHC(O)CH_3$, or $S(O_2)NH_2$; $R^i$ is H, methyl, ethyl, or acetyl, and q is 0, 1, or 2.

13. The method of claim 12, wherein Rg is methyl or methoxy; R' is H; and q is 0.

14. The method of claim 12, wherein U is N and V is CH.

15. The method of claim 14, wherein Z is N and W is O.

16. The method of claim 15, wherein X is $NR^c$; and $R^c$ is H, methyl, ethyl, or acetyl.

17. The method of claim 16, wherein Y is O or $CH_2$; and n is 0, 1, 2, 3, or 4.

18. The method of claim 17, wherein $R_3$ is aryl or heteroaryl.

19. The method of claim 18, wherein $R_3$ is pyridinyl.

20. The method of claim 12, wherein Y is O or $CH_2$, and n is 0, 1, 2, 3, or 4.

21. The method of claim 20, wherein $R_3$ is aryl or heteroaryl.

22. The method of claim 20, wherein $R_3$ is pyridinyl.

23. The method of claim 1, wherein $R_1$ is aryl or heteroaryl.

24. The method of claim 1, wherein the compound is selected from the group consisting of:

Compound 1:

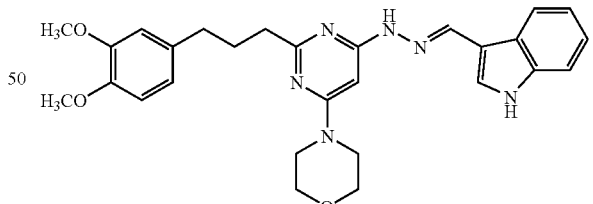

Compound 2:

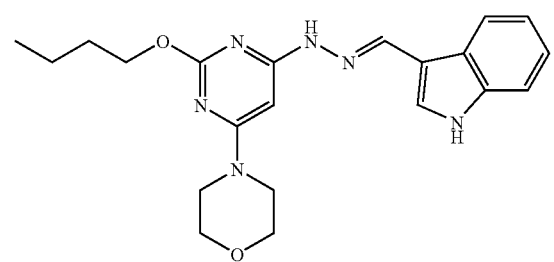

Compound 3:
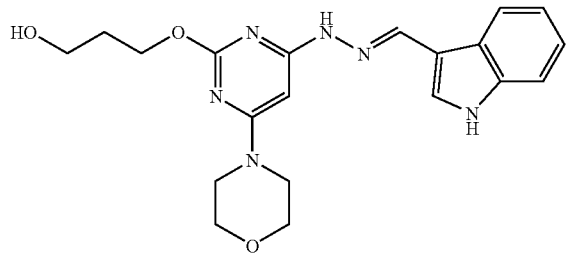
Compound 4:
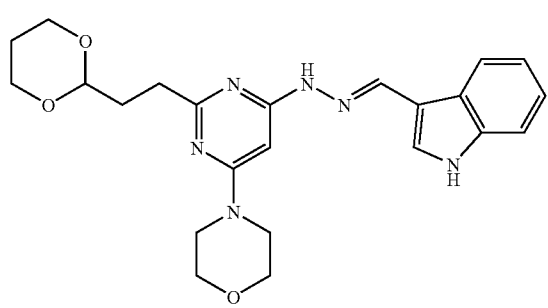
Compound 5:
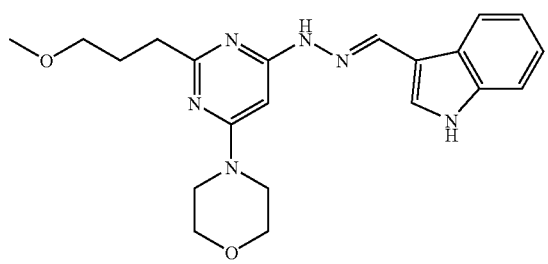
Compound 6:
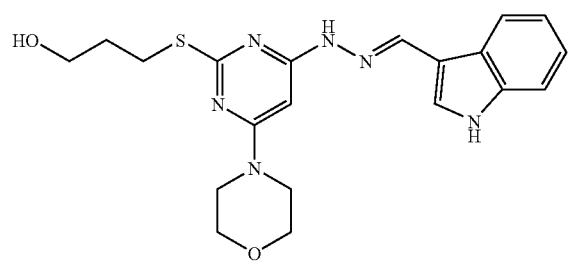
Compound 7:
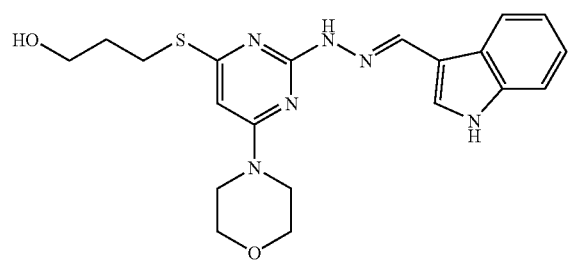
Compound 8:
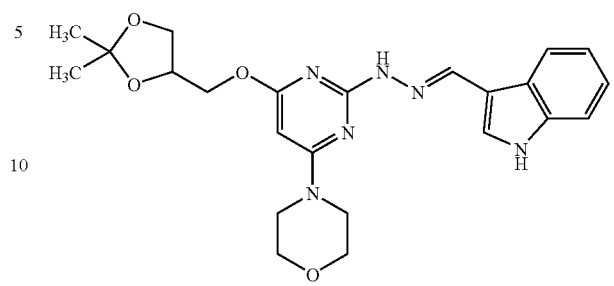
Compound 9:
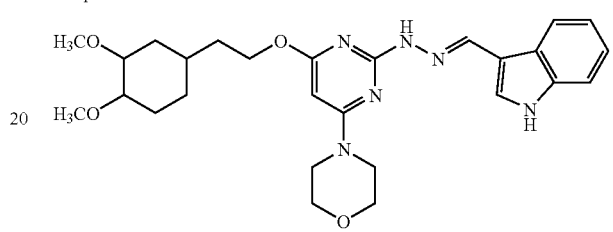
Compound 10:
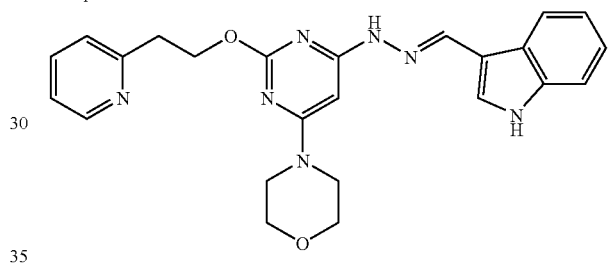
Compound 12:
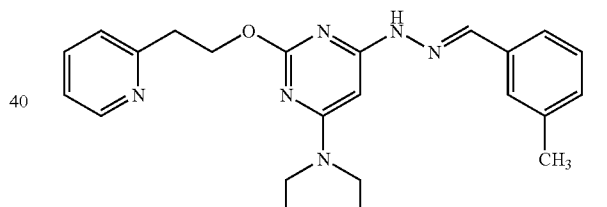
Compound 13:
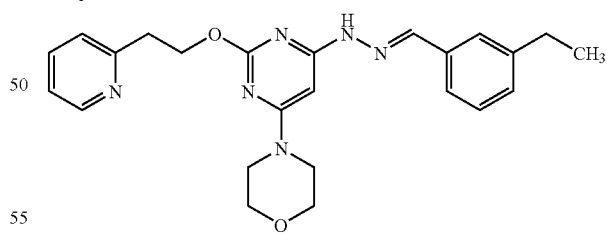
Compound 14:
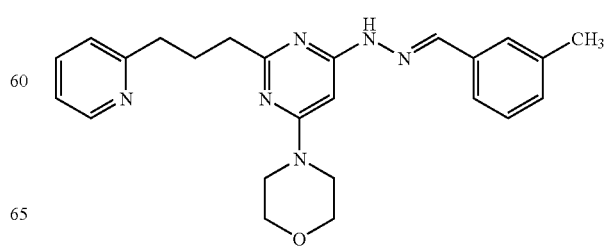

-continued
Compound 15:
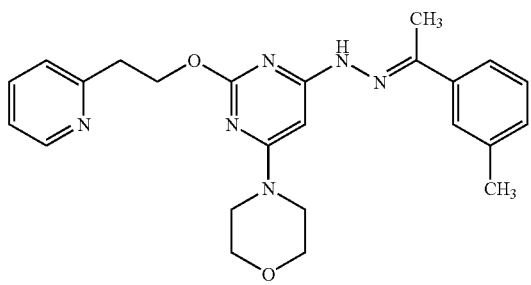
Compound 20:
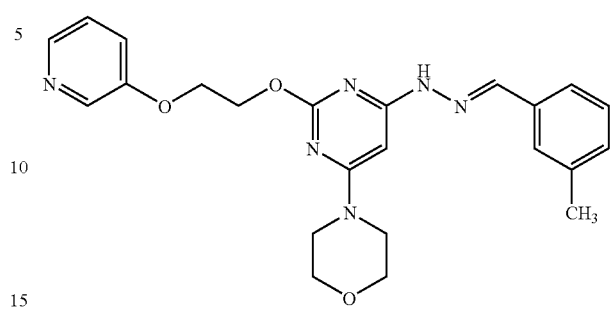
Compound 16:
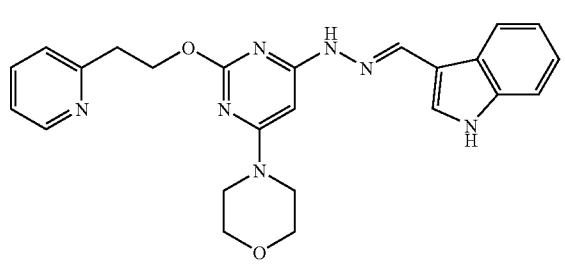
Compound 21:
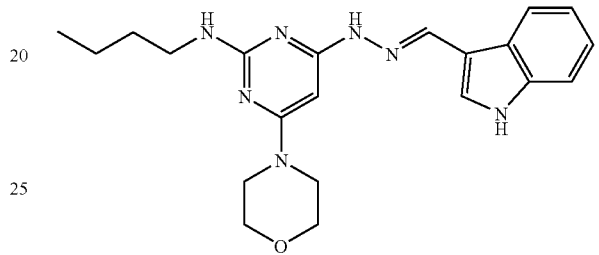
Compound 17:
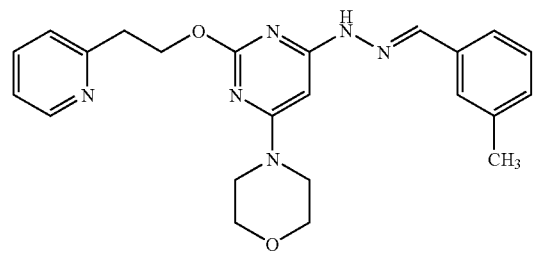
Compound 22:
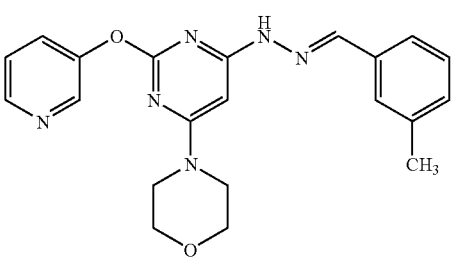
Compound 18:
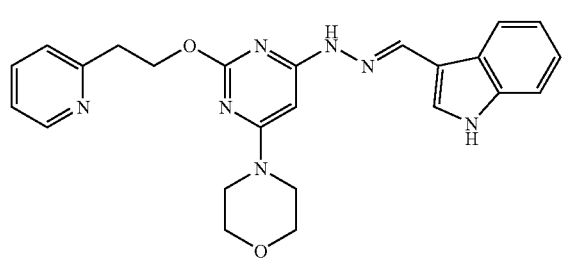
Compound 23:
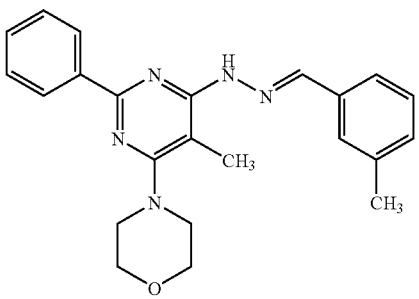
Compound 19:
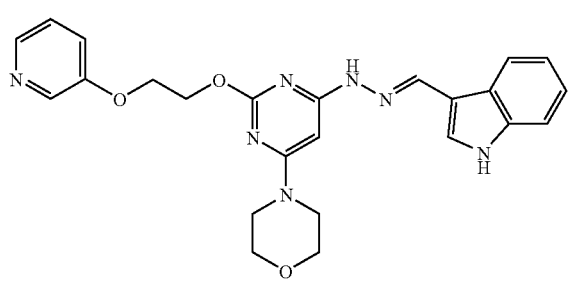
Compound 24:
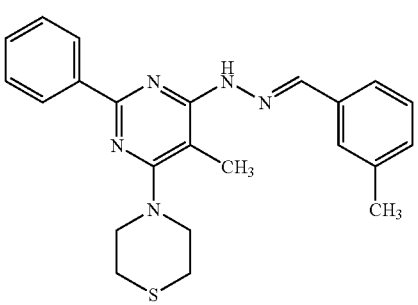

-continued
Compound 25:
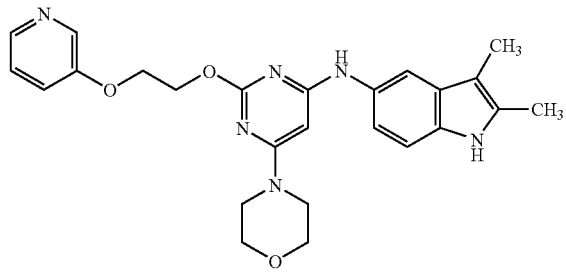
Compound 26:
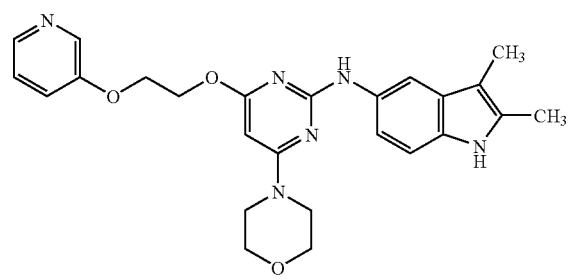
-continued
Compound 27:
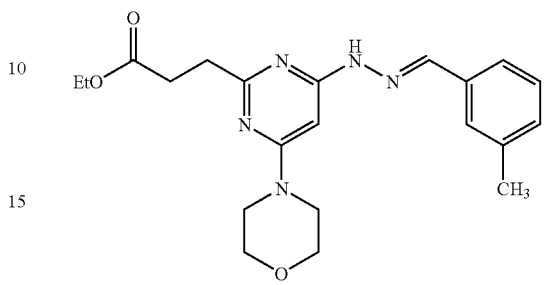
and pharmaceutically acceptable salts thereof.
* * * * *